United States Patent
Gupta et al.

(10) Patent No.: US 10,575,788 B2
(45) Date of Patent: Mar. 3, 2020

(54) COMPRESSIVE SENSING OF QUASI-PERIODIC SIGNALS USING GENERATIVE MODELS

(71) Applicants: Sandeep Gupta, Phoenix, AZ (US); Ayan Banerjee, Mesa, AZ (US)

(72) Inventors: Sandeep Gupta, Phoenix, AZ (US); Ayan Banerjee, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 266 days.

(21) Appl. No.: 15/787,534

(22) Filed: Oct. 18, 2017

(65) Prior Publication Data

US 2018/0103911 A1    Apr. 19, 2018

Related U.S. Application Data

(60) Provisional application No. 62/409,678, filed on Oct. 18, 2016.

(51) Int. Cl.
    *A61B 5/00*         (2006.01)
    *A61B 5/0404*     (2006.01)
    (Continued)

(52) U.S. Cl.
    CPC .......... *A61B 5/7232* (2013.01); *A61B 5/0006* (2013.01); *A61B 5/0404* (2013.01);
    (Continued)

(58) Field of Classification Search
    CPC ... A61B 5/7232; A61B 5/0006; A61B 5/0404; A61B 5/0432; A61B 5/0456; A61B 5/681
    (Continued)

(56) References Cited

U.S. PATENT DOCUMENTS

| | | | |
|---|---|---|---|
| 9,619,213 B2 | 4/2017 | Gupta et al. | |
| 9,626,521 B2 | 4/2017 | Gupta et al. | |
| (Continued) | | | |

OTHER PUBLICATIONS

Abdulghani et al., "Compressive Sensing Scalp EEG Signals: implementations and practical performance" Medical & Biological Engineering & Computing, 50(11):1137-1145, 2012.

(Continued)

*Primary Examiner* — Carl H Layno
*Assistant Examiner* — Erin M Piateski
(74) *Attorney, Agent, or Firm* — Michael Best & Friedrich LLP

(57) ABSTRACT

Methods and systems are described for sensing and recovery of a biological signal using generative-model-based compressive sensing. A transformation is applied to sparsify the quasi-periodic signal removing morphology parameters and leaving temporal parameters. The sparsified signal is sampled and the sampled signal data is transmitted to a base station. A homotopy recovery algorithm is applied to the received sampled signal data by the base station to recover the temporal parameters of the biological signal. Generative modelling is applied using previously captured morphology parameters to generate a reconstructed signal. Finally, the reconstructed signal is adjusted and scaled based on the recovered temporal parameters to provide a reconstructed signal that is diagnostically equivalent to the original biological signal.

23 Claims, 12 Drawing Sheets

(51) Int. Cl.

| | |
|---|---|
| A61B 5/0456 | (2006.01) |
| A61B 5/0432 | (2006.01) |
| A61B 5/0452 | (2006.01) |
| A61B 5/04 | (2006.01) |
| G16H 50/20 | (2018.01) |
| G16H 40/63 | (2018.01) |

(52) U.S. Cl.
CPC ...... *A61B 5/04011* (2013.01); *A61B 5/04014* (2013.01); *A61B 5/0432* (2013.01); *A61B 5/0456* (2013.01); *A61B 5/04525* (2013.01); *A61B 5/6823* (2013.01); *A61B 5/7264* (2013.01); *A61B 5/7275* (2013.01); *A61B 5/7278* (2013.01); *G16H 40/63* (2018.01); *G16H 50/20* (2018.01); *A61B 5/681* (2013.01); *A61B 2560/0209* (2013.01); *A61B 2562/04* (2013.01)

(58) Field of Classification Search
USPC .......................................................... 600/521
See application file for complete search history.

(56) References Cited

U.S. PATENT DOCUMENTS

| | | | |
|---|---|---|---|
| 9,642,543 B2 | 5/2017 | Banerjee et al. | |
| 9,706,963 B2 | 7/2017 | Gupta et al. | |
| 10,073,701 B2 | 9/2018 | Markovic et al. | |
| 10,342,447 B2 | 7/2019 | Banerjee et al. | |
| 2008/0001735 A1* | 1/2008 | Tran .................... | G06F 19/3418 340/539.22 |
| 2012/0148128 A1* | 6/2012 | Chefd'hotel ..... | G01R 33/56366 382/131 |
| 2013/0317377 A1 | 11/2013 | Gupta et al. | |
| 2014/0296678 A1* | 10/2014 | Mittal ................. | A61B 5/0022 600/372 |
| 2017/0086696 A1* | 3/2017 | Chen .................... | A61B 5/0006 |
| 2018/0189678 A1 | 7/2018 | Gupta et al. | |
| 2018/0300487 A1 | 10/2018 | Gupta et al. | |

OTHER PUBLICATIONS

Addison, "Wavelet transforms and the ECG: a review" Physiological measurement, 26(5):R155, 2005.
Agante et al. "ECG Noise Filtering using Wavelets with Soft-thresholding Methods" Computers in Cardiology, 1999, pp. 535-538, IEEE, 1999.
Aharon et al. "K-SVD: An Algorithm for Designing Overcomplete Dictionaries for Sparse Representation" IEEE Transactions on Signal Processing, 54(11):4311-4322, 2006.
Ahmed et al. "Electrocardiographic Data Compression via Orthogonal Transforms" IEEE Transactions on Biomedical Engineering, (6):484-487, 1975.
Allard et al. "Multi-scale geometric methods for data sets ii: Geometric multi-resolution analysis" Applied and Computational Harmonic Analysis, 32(3):435-462, 2012.
Baheti et al. "An ultra low power pulse oximeter sensor based on compressed sensing" Wearable and Implantable Body Sensor Networks, 2009. BSN 2009. Sixth International Workshop, pp. 144-148, Jun. 2009.
Banerjee et al. "Challenges of Implementing Cyber-physical Security Solutions in Body Area Networks" In BodyNets 09: Proceedings of International Conference on Body Area Networks, 2009.
Banerjee et al. "Ensuring Safety, Security, and Sustainability of Mission-Critical Cyber-Physical Systems" Proceedings of the IEEE, 100(1):283-299, Jan. 2012.
Banerjee et al. "Health-Dev: Model Based Development of Pervasive Health Monitoring Systems" Wearable and Implantable Body Sensor Networks (BSN), 2012 Ninth International Conference, pp. 85-90, May 2012.
Banerjee et al. "Clinical Evaluation of Generative Model Based Monitoring and Comparison with Compressive Sensing" In Proceedings of the Conference on Wireless Health, WH '15, pp. 1:1-1:8, New York, NY, USA, 2015. ACM.
Banerjee et al. "Tackling new frontiers in modeling and analysis of cyber-physical systems" In 1 st workshop on Cyber—Physical Systems Education, 2013.
Baraniuk et al. "Model-based compressive sensing" Information Theory, IEEE Transactions, 56(4):1982-2001, Apr. 2010.
Baraniuk et al. "Random projections of smooth manifolds" Found. Comput. Math., 9(1):51-77, Jan. 2009.
Bosworth et al. "High-speed flow imaging utilizing spectral-encoding of ultrafast pulses and compressed sensing" Lasers and Electro-Optics (CLEO), 2014 Conference, pp. 1-2, Jun. 2014.
Bosworth et al. "High-speed compressed sensing measurement using spectrally-encoded ultrafast laser pulses" Information Sciences and Systems (CISS), 2015 49th Annual Conference, pp. 1-4, Mar. 2015.
Candes et al. "An introduction to compressive sampling" IEEE Signal Processing Magazine, 25(2):21-30, 2008.
Chartrand et al. "Iteratively reweighted algorithms for compressive sensing" IEEE international conference on Acoustics, speech and signal processing (ICASSP), pp. 3869-3872 IEEE, 2008.
Chen et al. "Multiscale geometric wavelets for the analysis of point clouds" 44th Annual Conference on Information Sciences and Systems (CISS), pp. 1-6. IEEE, 2010.
Chen et al. "Multiscale geometric and spectral analysis of plane arrangements" IEEE Conference on Computer Vision and Pattern Recognition (CVPR), pp. 2825-2832. IEEE, 2011.
Chen et al. "Compressive sensing on manifolds using a nonparametric mixture of factor analyzers: Algorithm and Performance Bounds" IEEE Transactions on Signal Processing, 58(12):6140-6155, Dec. 2010.
Chen et al. "Atomic decomposition by basis pursuit" SIAM journal on Scientific Computing, 20(1):33-61, 1998.
CIDSE Arizona State University. Consortium of embedded systems. http://embedded.asu.edu/.
Davenport et al. "Introduction to compressed sensing" Compressed Sensing: Theory and Applications. Cambridge University Press, 2011.
Donoho "Compressed sensing" IEEE Transactions on Information Theory, vol. 52, No. 4 pp. 1289-1306, 2006.
Dremeau et al. "Boltzmann machine and mean-field approximation for structured sparse decompositions" IEEE Transactions on Signal Processing, vol. 60 No. 7, Jul. 2012 pp. 3425-3438.
Gang et al. "Generative modeling of temporal signal features using hierarchical probabilistic graphical models" Digital Signal Processing Workshop and IEEE Signal Processing Education Workshop (DSP/SPE), 2011 IEEE, pp. 307-312, Jan 2011.
Garrigues et al. "An homotopy algorithm for the lasso with online observations" Proc. NIPS, 2008.
Goodman et al. "Efficient reconstruction of block-sparse signals" Statistical Signal Processing Workshop (SSP), 2011 IEEE, pp. 629-632, Jun. 2011.
He et al. "Exploiting structure in wavelet-based bayesian compressive sensing" IEEE Transactions on Signal Processing, vol. 57 No. 9. pp. 3488-3497, Sep. 2009.
Hegde et al. "Nearly linear-time model-based compressive sensing" In Javier Esparza, Pierre Fraigniaud, Thore Husfeldt, and Elias Koutsoupias, editors, Automata, Languages, and Programming, vol. 8572 of Lecture Notes in Computer Science, pp. 588-599. Springer Berlin Heidelberg, 2014.
Hegde et al. "Numax: A convex approach for learning near-isometric linear embeddings" IEEE Transactions on Signal Processing, vol. 63 No. 22, Nov. 2015.
Hinton et al. "Inferring motor programs from images of handwritten digits" Advances in Neural Information Processing Systems 18 [Neural Information Processing Systems, NIPS 2005, Dec. 5-8, 2005, Vancouver, British Columbia, Canada], pp. 515-522, 2005.
Impact Lab. 1st international workshop on mobile medical applications held in conjunction with sensys. http://sensys.acm.org/2014/workshops/, 2014.

(56) References Cited

OTHER PUBLICATIONS

Impact Lab. Tutorial on mobile medical applications held in conjunction with bsn. http://www.bs.2014.org/?id=5#workshop2, 2014.
Ince et al. "Nonconvex compressed sensing with partially known signal support" Signal Processing, 93, pp. 338-344, 2013.
Indyk et al. "K-median clustering, model-based compressive sensing, and sparse recovery for earth mover distance" Proceedings of the Forty-third Annual ACM Symposium on Theory of Computing, STOC '11, pp. 627-636, Jun. 2011, ACM.
Jones et al. "Impact of compressed sensing on clinically relevant metrics for ambulatory ECG monitoring" Electronics Letters, vol. 51 No. 4. pp. 323-325, Feb. 2015.
Khajehnejad et al. "Analyzing weighted l1 minimization for sparse recovery with nonuniform sparse models" IEEE Transactions on Signal Processing, vol. 59 No. 5, pp. 1985-2001, May 2011.
Kreutz-Delgado et al. "Dictionary learning algorithms for sparse representation" Neural computation, 15(2):349-396, 2003.
Liu et al. "Energy efficient telemonitoring of physiological signals via compressed sensing: A fast algorithm and power consumption evaluation" Biomedical Signal Processing and Control, 11, pp. 80-88, 2014.
Mairal et al. "Online dictionary learning for sparse coding" Proceedings of the 26th Annual International Conference on Machine Learning, pp. 689-696. ACM, 2009.
Mamaghanian et al. "Compressed sensing for real-time energy-efficient ecg compression on wireless body sensor nodes" IEEE Transactions on Biomedical Engineering, vol. 58 No. 9, pp. 2456-2466, 2011.
McSharry et al. "A dynamical model for generating synthetic electrocardiogram signals" IEEE Transactions on Biomedical Engineering, vol. 50 No. 3, pp. 289-294, 2003.
Nabar et al. "GeM-REM: Generative modeldriven resource efficient ECG monitoring in body sensor networks", International Conference on Body Sensor Networks, pp. 1-6, May 2011.
Needell et al. "Uniform uncertainty principle and signal recovery via regularized orthogonal matching pursuit" Foundations of Computational Mathematics, vol. 9 No. 3, pp. 317-334, 2009.
Ohlsson et al. "Nonlinear basis pursuit" Asilomar Conference on Signals, Systems and Computers, 2013, pp. 115-119, Nov. 2013.
Polak et al. "Recovery of sparse signals from amplitudelimited sample sets" IEEE International Conference on Acoustics, Speech and Signal Processing, pp. 4663-4667, May 2013.
Bashar Rajoub et al. "An efficient coding algorithm for the compression of ecg signals using the wavelet transform" IEEE Transactions on Biomedical Engineering, vol. 49 No. 4, pp. 355-362, 2002.
Ren, "A Scalable VLSI Architecture for Real-Time and Energy-Efficient Sparse Approximation in Compressive Sensing Systems" Submitted Dissertation to the University of California—Los Angeles, (127 pages) Jan. 2015.
Ren et al. "A Single-Precision Compressive Sensing Signal Reconstruction Engine on FPGAS" In Proceedings of the 23rd International Conference on Field Programmable Logic and Applications, pp. 1-4. IEEE, Sep. 2013.
Ren et al. "A configurable 12-to-237ks/s 12.8 mw Sparse-Approximation Engine for Mobile Data Aggregation of Compressively Sampled Physiological Signals" Proceedings of the 2015 IEEE International Solid-State Circuits Conference pp. 1-3. IEEE, Feb. 2015.
Ren et al. "A configurable 12-to-237ks/s 12.8mw sparse-approximation engine for mobile data aggregation of compressively-sampled physiological signals" IEEE Journal of Solid State Circuits, (to appear), Jan. 2016.
Ren et al. "Scalable and parameterised vlsi architecture for efficient sparse approximation in fpgas and socs" IET Electronics Letters, vol. 49 No. 23, pp. 1440-1441, Nov. 2013.
Ren et al. A square-Root-Free Matrix Decomposition mMthod for Energy-Efficient Least Square Computation on Embedded Systems, IEEE Embedded Systems Letters, vol. 6 No. 4, pp. 73-76, Aug. 2014.

Salakhutdinov "Learning Deep Generative Models" PhD thesis, Submitted to the University of Toronto, Ont., Canada, 2009. AAINR61080.
Shahrasbi et al. "TC-CSBP: Compressive sensing for time-correlated data based on belief propagation" Information Sciences and Systems (CISS), 2011 45th Annual Conference, pp. 1-6, Mar. 2011.
Thakor et al. "Applications of adaptive filtering to ecg analysis: noise cancellation and arrhythmia detection" IEEE Transactions on Biomedical Engineering, vol. 38 No. 8, pp. 785-794, 1991.
Tropp et al. "Signal recovery from random measurements via orthogonal matching pursuit" IEEE Transactions on Information Theory, vol. 53 No. 12, pp. 4655-4666, 2007.
Venkatasubramanian et al. "Green and sustainable cyber-physical security solutions for body area networks" Body Sensor Networks 2009: Proceedings of the 2009 Sixth International Workshop on Wearable and Implantable Body Sensor Networks, pp. 240-245, IEEE Computer Society.
Venkatasubramanian et al. "EKG-based key agreement in body sensor networks" Computer Communications Workshops, 2008. INFOCOM. IEEE, pp. 1-8, Apr. 2008.
Venkatasubramanian et al. "PSKA: Usable and Secure Key Agreement Scheme for Body Area Networks" IEEE Transactions on Information Technology in Biomedicine, vol. 14, No. 1, Jan. 2010 pp. 60-68.
Venkatasubramanian et al. "Physiological Value Based Efficient Usable Security Solutions for Body Sensor Networks" ACM Transactions on Sensor Networks, vol. 6. No. 4, Article 31, Jul. 2010.
Venkatasubramanian et al. "Plethysmogram-based secure intersensor communication in body area networks" Military Communications Conference, 2008. MILCOM 2008. IEEE, pp. 1-7, Nov. 2008.
Vorobyov et al. "Blind noise reduction for multisensory signals using ICA and subspace filtering, with application to EEG analysis" Biological Cybernetics, vol. 86 No. 4, pp. 293-303, 2002.
Wu et al. "Compressive sensing-based signal compression and recovery in UWB wireless communication system" Wireless Communications and Mobile Computing, 14(13)1266-1275, 2014.
Xu et al. "An energy-efficient compressive sensing framework incorporating adaptive dictionary learning for long-term wireless health monitoring" IEEE International Conference on Acoustics, Speech and Signal Processing, volume in preparation, 2016.
Yap et al. "Stable manifold embeddings with operators satisfying the restricted isometry property" Information Sciences and Systems, 2011 45th Annual Conference, pp. 1-6, Mar. 2011.
Yenduri et al. "A low-power compressive sampling time-based analog-to-digital converter" Emerging and Selected Topics in Circuits and Systems, IEEE Journal, vol. 2 No. 3 pp. 502-515, Sep. 2012.
Zhang et al. "Spatiotemporal sparse bayesian learning with applications to compressed sensing of multichannel physiological signals" IEEE Transactions on Neural Systems and Rehabilitation Engineering, vol. 22 No. 6, pp. 1186-1197, Nov. 2014.
Zhang et al. "Compressed sensing for energy-efficient wireless telemonitoring of noninvasive fetal ECG via block sparse bayesian learning" IEEE Transactions on Biomedical Engineering, vol. 60 No. 2, pp. 300-309, Feb. 2013.
Zhang et al. "Compressed sensing for energy-efficient wireless telemonitoring: Challenges and opportunities" In Signals, Systems and Computers, 2013 Asilomar Conference, pp. 80-85, Nov. 2013.
Zigel et al. "The weighted diagnostic distortion (WDD) measure for ECG signals compression" IEEE Transactions on Biomedical Engineering, vol. 47 No. 11, pp. 1422-1430, 2000.
Huang et al. "Weardrive: Fast and energy-efficient storage for wearables" 2015 USENIX Annual Technical Conference, pp. 613-625, Santa Clara, CA, Jul. 2015.
Shukla et al. "Row-sparse blind compressed sensing for reconstructing multi-channel fEEGg signals" Biomedical Signal Processing and Control, 18:174-178, 2015.
Yang et al. "Fast 1-minimization algorithms for robust face recognition" IEEE Transactions on Image Processing, vol. 20 No. 8, pp. 3234-3246, 2013.

(56) References Cited

OTHER PUBLICATIONS

Lopes, "Estimating Unknown Sparsity in Compressed Sensing", Proceedings of the 30th International Conference on Machine Learning (Atlanta, GA, Jun. 16, 2013), 2013, vol. 28, pp. III-217-III-225.

Mahrous et al., "Block Sparse Compressed Sensing of Electroencephalogram (EEG) Signals by Exploiting Linear and Non-Linear Dependencies", Sensors, Feb. 2016, vol. 16, No. 2, article 201, 16 pages <DOI:10.3390/s16020201>.

Wang, et al., "Data-Driven Sampling Matrix Boolean Optimization for Energy-Efficient Biomedical Signal Acquisition by Compressive Sensing", IEEE Transactions on Biomedical Circuits and Systems, Apr. 2017 [IEEE date of publication Nov. 2016], vol. 11, No. 2, pp. 255-266, <DOI:10.1109/TBCAS.2016.2597310>.

Xu et al., "A data-driven compressive sensing framework tailored for energy-efficient wearable sensing", 2017 IEEE International Conference on Acoustics, Speech and Signal Processing (ICASSP) (New Orleans, LA, Mar. 5-9, 2017), added to IEEE Xplore Jun. 2017, pp. 861-865, <DOI:10.1109/ICASSP.2017.7952278>.

Xu et al., "CSVideoNet: A Real-Time End-to-End Learning Framework for High-Frame-Rate Video Compressive Sensing", 2018 IEEE Winter Conference on Applications of Computer Vision (WACV) (Lake Tahoe, NV, Mar. 12-15, 2018), added to IEEE Xplore May 2018, pp. 1680-1688, <DOI:10.1109/WACV.2018.00187>.

Yi et al., "Nonlinear compressed sensing based on composite mappings and its pointwise linearization", arXiv, submitted Jun. 2015, 16 pages, retrieved from the internet: <URL:https://arxiv.org/abs/1506.02212>.

Yu et al., "Bayesian compressive sensing for cluster structured sparse signals", Signal Processing, Jan. 2012 [available online Jul. 2011], vol. 92, No. 1, pp. 259-269, <DOI:10.1016/j.sigpro.2011.07.015>.

Zhang et al., "An improved compressive sensing reconstruction algorithm using linear/non-linear mapping", 2011 Information Theory and Applications Workshop (La Jolla, CA, Feb. 6-11, 2011), added to IEEE Xplore Apr. 2011, 7 pages.

Banerjee et al., "Clinical Evaluation of Generative Model Based Monitoring and Comparison with Compressive Sensing" PowerPoint presentation to Wireless Health Conference, 2015, (14 slides).

\* cited by examiner

| | Diagnostic features | Definition | GeMREM error | CS error |
|---|---|---|---|---|
| Temporal Parameters | mean R-R interval | time between two consecutive R peaks | 88th percentile ≤ 5% | 100th percentile ≤ 5% |
| | R-R interval std | standard deviation of R-R interval | 84th percentile ≤ 10% | 92nd percentile ≤ 10% |
| | lhf ratio | ratio of signal power in low to high frequency | 76th percentile ≤ 10% | 72nd percentile ≤ 10% |
| Morphology Parameters | QRS width | time between Q peak and S peak | 100th percentile ≤ 2% | 72nd percentile ≤ 2% |
| | QRS height | maximum amplitude in QRS complex | 100th percentile ≤ 5% | 48th percentile ≤ 5% |
| | QRS trough | minimum amplitude in QRS complex | 92nd percentile ≤ 5% | 64th percentile ≤ 5% |
| | P wave amplitude | height of P peak | 84th percentile ≤ 5% | 76th percentile ≤ 5% |
| | T wave amplitude | height of T peak | 96th percentile ≤ 5% | 88th percentile ≤ 5% |
| | P wave duration | time between start and end of P wave | 88th percentile ≤ 5% | 64th percentile ≤ 5% |
| | T wave duration | time between start and end of T wave | 100th percentile ≤ 5% | 76th percentile ≤ 5% |

FIG. 3

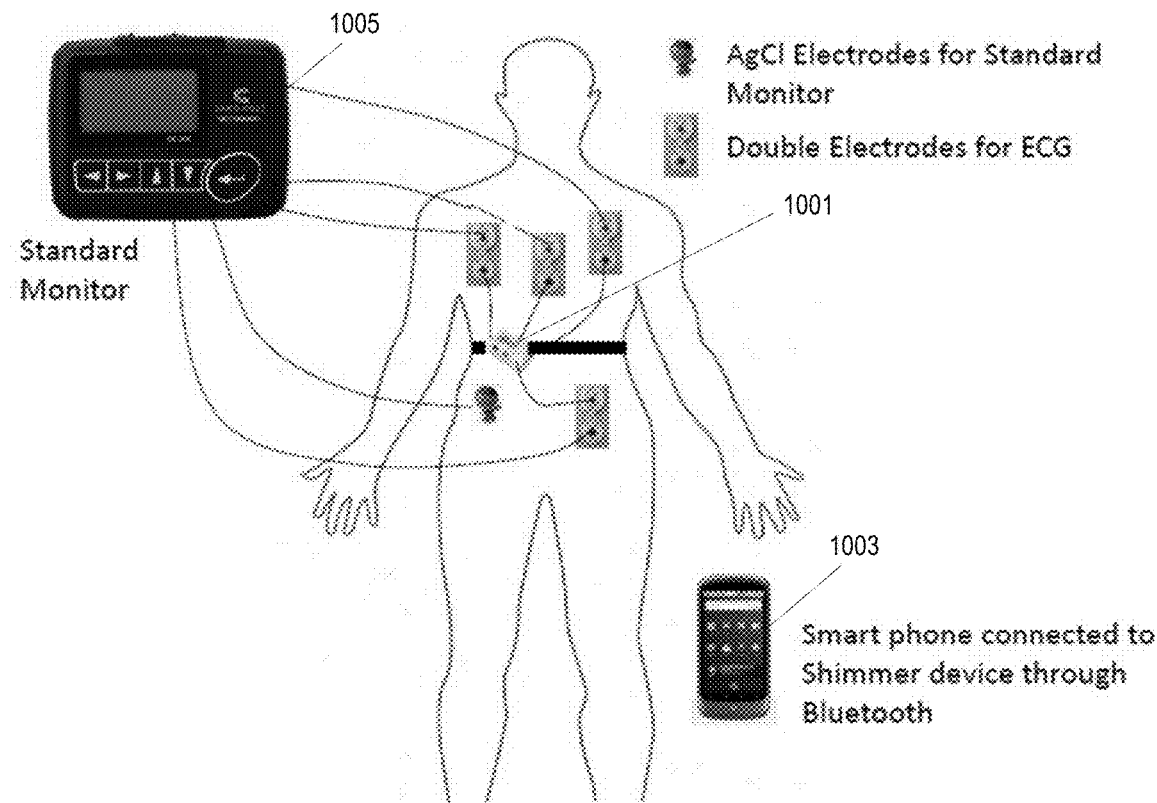

FIG. 10

| Shape features | GenCS error | CS error |
|---|---|---|
| QRS width | $100^{th}$ percentile $\leq 2\%$ | $45^{nd}$ percentile $\leq 2\%$ |
| QRS height | $100^{th}$ percentile $\leq 5\%$ | $20^{th}$ percentile $\leq 5\%$ |
| QRS trough | $92^{nd}$ percentile $\leq 5\%$ | $41^{th}$ percentile $\leq 5\%$ |
| P wave amplitude | $84^{th}$ percentile $\leq 5\%$ | $30^{th}$ percentile $\leq 5\%$ |
| T wave amplitude | $96^{th}$ percentile $\leq 5\%$ | $44^{th}$ percentile $\leq 5\%$ |
| P wave duration | $88^{th}$ percentile $\leq 5\%$ | $45^{th}$ percentile $\leq 5\%$ |
| T wave duration | $100^{th}$ percentile $\leq 5\%$ | $60^{th}$ percentile $\leq 5\%$ |

FIG. 12

COMPRESSIVE SENSING OF QUASI-PERIODIC SIGNALS USING GENERATIVE MODELS

RELATED APPLICATIONS

This application claims the benefit of U.S. Provisional Patent Application No. 62/409,678, filed Oct. 18, 2017, and entitled "COMPRESSIVE SENSING OF QUASI-PERIODIC SIGNALS USING GENERATIVE MODELS," the entire contents of which are incorporated herein by reference.

STATEMENT REGARDING FEDERALLY SPONSORED RESEARCH

This invention was made with government support under R21 EB019202 awarded by the National Institutes of Health. The government has certain rights in the invention.

BACKGROUND

The present invention relates to systems and methods for monitoring biological signals (for example, ECG signals) in "free living" conditions.

SUMMARY

Continuous cardiac monitoring in free living conditions is useful for diagnosis of diseases, evaluation of post-operative progress, and also for general physical health and wellbeing. For instance, continuous cardiac monitoring can be used in exercise applications to provide accurate estimate of calories burnt in an exercise bout. However, a free living scenario imposes a number of significant unsolved challenges. In some implementations, wearable cardiac sensors sense data at a recommended sampling rate (e.g., a Nyquist rate) and transfer it to the smartphone through Bluetooth. The smartphone runs processing algorithms to recover the data and either displays the data or runs one or more diagnostic algorithms. The smartphone is used as an intermediate storage and computation hub, before the data is stored in the cloud server. However, in a free living condition for instance when the user is exercising, the user may not have the smartphone in close proximity to the wearable sensor. Hence, the connection between smartphone and the wearable sensor can be intermittent possibly resulting in monitoring interruptions at critical times.

The introduction of smartwatches as wearable alternatives to smartphones, may improve continuous monitoring since it is more easily worn along with the cardiac sensors and hence always within communication range of the sensor. The watch can act as an emergency source of storage and computation when the smartphone is not available. However, the computation, storage, and battery constraints of the smartwatch impose limitations on its usage as display and data recovery hub. In some implementations, the smartwatch is used only during scenarios when the smartphone is not nearby. Compression techniques that enable sensing at lower frequencies than theoretically required and reduce communication through the usage of signal models can potentially facilitate continuous cardiac monitoring during free living conditions. By reducing the sample size, the execution time of the data processing algorithms might also be reduced.

Two examples of compression techniques include a) compressive sensing (CS) that allows accurate recovery of signals with fewer samples than Nyquist rate and b) generated model based resource efficient monitoring (GeMREM), which compares a signal with a pre-learned model and reduces data transmission if signal matches model. On one hand CS provides sensing reduction but has a complex recovery method, which makes it inefficient with respect to energy and storage requirements when implemented in a smartwatch or a smartphone. On the other hand, GeMREM provides no sensing reduction and requires the sensor to process the data and match with a model, but it gives orders of magnitude more communication reduction than CS and has a relatively simple recovery algorithm. The lightweight recovery algorithm enables resource efficient execution of GeMREM in a smartwatch or smartphone.

Various embodiments of the invention as described herein combine the notion of CS and GeMREM to provide a novel generative model based compressive sensing (GenCS), which provides high order of sensing compression with simple sensors, and resource efficient recovery. In some embodiments, the GenCS method is implemented using Shimmer2r sensors, an android smartwatch, and a Nexus 5 smartphone.

In one embodiment, the invention provides a method for sensing and recovery of a biological signal. A transformation is applied to sparsify the biological signal removing morphology parameters and leaving temporal parameters. The sparsified signal is sampled and the sampled signal data is transmitted to a base station. A homotopy recovery algorithm is applied to the received sampled signal data by the base station to recover the temporal parameters of the biological signal. Generative modelling is applied using previously captured morphology parameters to generate a reconstructed signal. Finally, the reconstructed signal is adjusted and scaled based on the recovered temporal parameters to provide a reconstructed signal that is diagnostically equivalent to the original biological signal.

In another embodiment, the invention provides a monitoring system including a wearable sensor device with a sensor configured to detect the quasi-periodic signal and a wireless transmitter. The wearable sensor device is configured to apply a transformation to generate a sparsified signal based on the quasi-periodic signal. The sparsified signal includes termporal parameters of the quasi-periodic signal, but omits morphology parameters of the quasi-periodic signal. The wearable sensor device then samples the sparsified signal and transmits the sampled sparsified signal through the wireless transmitter to a base station device for recovery of the quasi-periodic signal.

In some embodiments, the base station is configured to receive the sampled sparsified signal and recover the temporal parameters of the quasi-periodic signal from the sampled sparsified signal. The base station then generates a reconstructed signal shape using previously captured/stored morphology parameters and generates a reconstructed signal by adjusting and scaling the reconstructed signal shape based on the recovered temporal parameters. In some embodiments, the reconstructed signal is diagnostically equivalent to the quasi-periodic signal.

Other aspects of the invention will become apparent by consideration of the detailed description and accompanying drawings.

BRIEF DESCRIPTION OF THE DRAWINGS

FIG. 3 is a table listing examples of temporal and morphology parameters in an ECG signal and statistics regarding the accuracy of recovery of those signal parameters using Compressive Sensing and Generative Modelling.

FIG. 10 is a schematic diagram of a signal monitoring system as used in one example.

FIG. 12 is a table of the accuracy of the GenCS method of FIG. 8 and a Compressive Sensing (CS) method in recovering ECG shape parameters.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
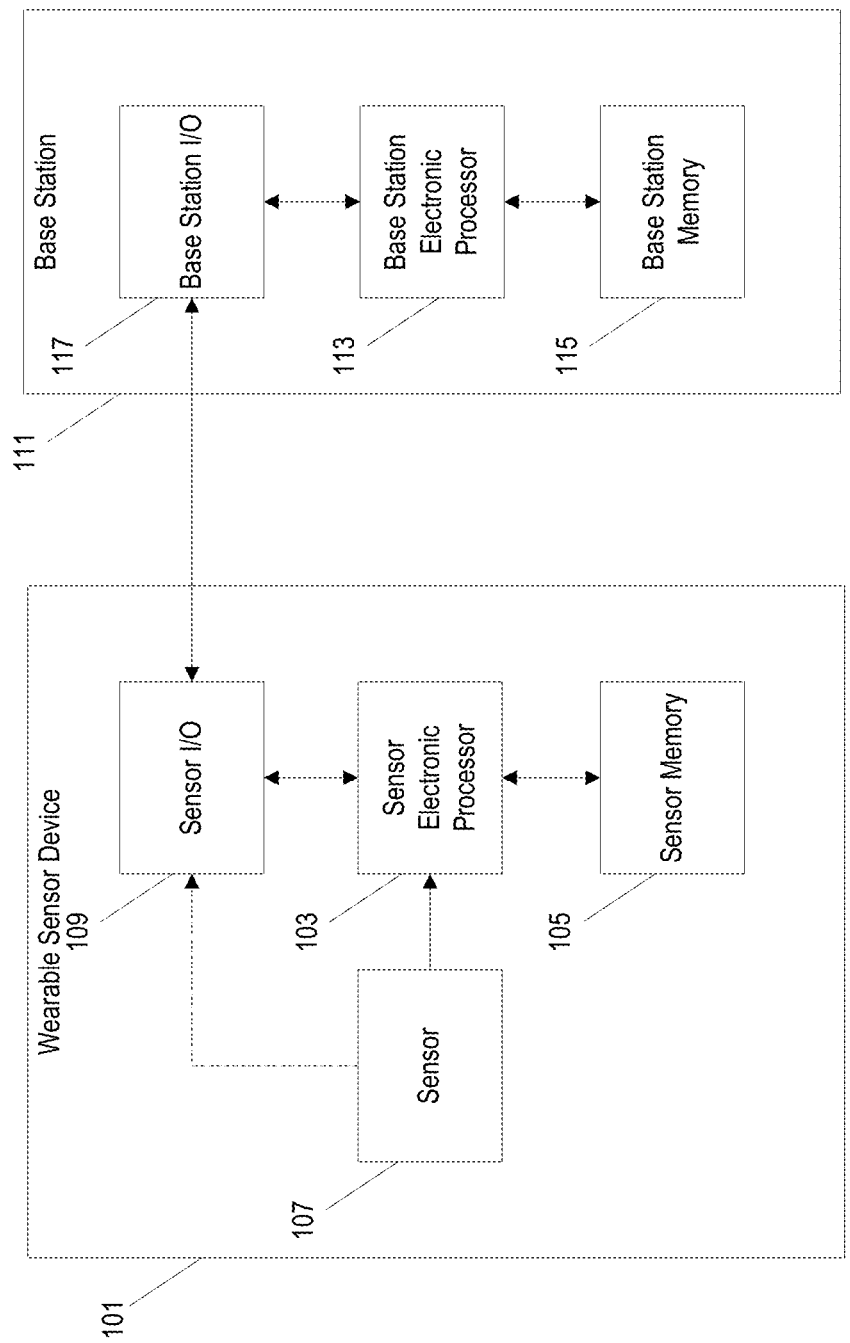
FIG. 1 is a block diagram of a signal monitoring system according to one embodiments.

FIG. 1 illustrates an example of a system for sensing biological signals under "free living" conditions. A wearable sensor device 101 includes a sensor electronic processor 103 and a sensor memory 105. The sensor memory 105 includes a non-transitory, computer-readable memory configured to store data and instructions that are executed by the sensor electronic processor 103 to provide functional operation of the wearable sensor device 101 (e.g., as described herein). The wearable sensor device 101 also includes a sensor 107 configured to capture biologic signal data and provides the sensed signal data to the sensor electronic processor 103 either directly or through a sensor input/output module 109.

In some implementations, the sensor input/output module 109 includes a wireless transmitter and the wearable sensor device 101 is configured to transmit signal information to a base station 111 through the sensor input/output module 109. The base station 111 includes a base station input/output module 117, including, for example, a wireless receiver (or transceiver), for receiving data from the signal sensor 101 and a base station electronic processor 113 and base station memory 115 for analyzing the received signal.

In some implementations, the sensor 107 is incorporated into the same housing/device as the rest of the wearable sensor device 101. However, in other implementations, the sensor 107 is a separate component worn by the user that is configured to transmit sensor data to the sensor electronic processor 103 through a wired or wireless communication channel. For example, the wearable sensor device 101 may include a wrist worn device with a sensor mounted on the underside in contact with the skin of the user. In another example, the sensor 107 can include one or more ECG sensor leads coupled to the user's body in wired communication with the sensor electronic processor, which may be housed, for example, in a belt pack or wrist-worn housing.

Figure 2A:
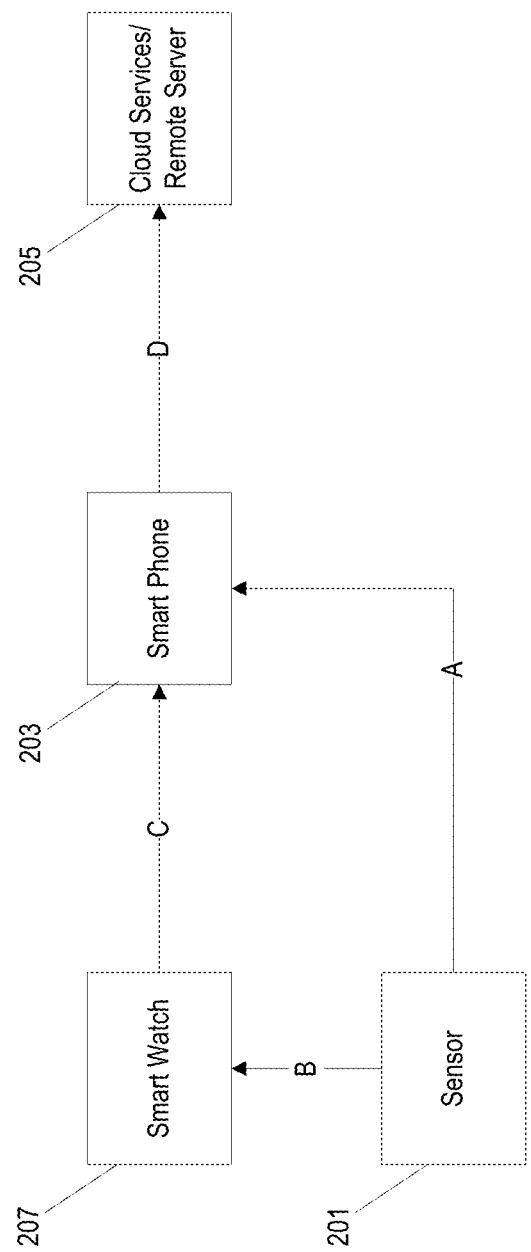
FIG. 2A is a functional block diagram of a signal monitoring system communicating with a base station with an intermediate communication device.

In some implementations (such as those examples discussed above), raw signal data is received, processed, and transmitted directly to the base station by the wearable sensor device. However, in other implementations, the wearable sensor device 101 may be configured to transmit the signal data to the base station through an intermediate communication device. In the example of FIG. 2A, a cardiac sensor device 201 is worn by the user to capture physiological data. The cardiac sensor device 201 is configured to transmit sensed signal data to a Smart Phone 203 (operating as the "base station"). Once the signal data is received by the Smart Phone 203, the Smart Phone 203 can upload the signal data to a cloud services and/or a remote server 205 for storage and, in some cases, further processing.

In this example, the cardiac sensor device 201 is equipped with a Bluetooth transceiver and, when the cardiac sensor device 201 is within range of the Smart Phone 203, it can communicate physiological signal data directly to the Smart Phone 203 (via wireless communication connection "A"). However, because the user might not always carry the Smart Phone 203—for example, while exercising—the Bluetooth connection between the cardiac sensor device 201 and the Smart Phone 203 can be intermittent, weak, or non-existent. Accordingly, in this example, the cardiac sensor device 201 is configured to transmit sensor data to the Smart Phone 203 through a Smart Watch 207 that is worn by the user (via wireless communication channel "B"). Because the Smart Watch 207 is worn by the same user as the wearable sensor device 201, a stronger and more reliable Bluetooth connection can often be established between the smart watch 207 and the wearable sensor device 201. Furthermore, the smart watch 207 may be configured to utilize other communication protocols in addition to Bluetooth including, for example, WiFi or 4G LTE to establish a wireless communication connection with the smart phone 203. In some situations and configurations, the smart watch 207 is able to establish wireless communication with the smart phone 203 even when the wearable sensor device 201 is unable to do so (e.g., when the user is not carrying the smart phone 203). The smart watch 207 relays the physiological signal data from the wearable sensor device 201 to the smart phone 203 (via wireless communication connection "C"). The smart phone 203 stores, processes, and displays data based on the receive physiological signal data and, in some implementations, further relays the information to a cloud services or a remote server 205 (via wireless communication channel "D").

In some implementations, a wearable sensor device (e.g., cardiac sensor device 201) may be configured to only communicate directly with a base station (e.g., smart phone 203). In some such implementations, the wearable sensor device may be configured to store some or all of the sensed signal data to a memory of the wearable sensor device until a wireless connection with the base station can be established (e.g., wireless communication link "A" in the example of FIG. 2A). Conversely, in other implementations, the wearable sensor device (e.g., cardiac sensor device 201) may be configured to only communication with the base station (e.g., smart phone 203) indirectly through an intermediate communication device that is also worn by the user (e.g., smart watch 207). In some of these implementations, the intermediate communication device may be configured to store some or all of the sensed signal data to a memory of the intermediate communication device until a wireless connection between the intermediate communication device and the base station (e.g., wireless communication connection "C" in the example of FIG. 2A) can be established.

In still other implementations, the wearable sensor device (e.g., the cardiac sensor device 201) may be configured to transmit sensed signal data directly to the base station (e.g., smart phone 203) when a wireless connection can be established directly with the base station (e.g., wireless communication connection "A" in FIG. 2A) and to transmit the sensed signal data to the intermediate communication device (e.g., smart watch 207) (e.g., via wireless communication connection "B" in FIG. 2A) when the wireless connection directly to the base station cannot be established. The intermediate communication device (e.g., smart watch 207) will then store the received signal data until a wireless connection can be established between the intermediate communication device (e.g., smart watch 207) and the base station (e.g., smart phone 203)—at which time the intermediate communication device would transmit the stored signal data to the base station (e.g., via wireless communication connection "C" in FIG. 2A).

Figure 2B:
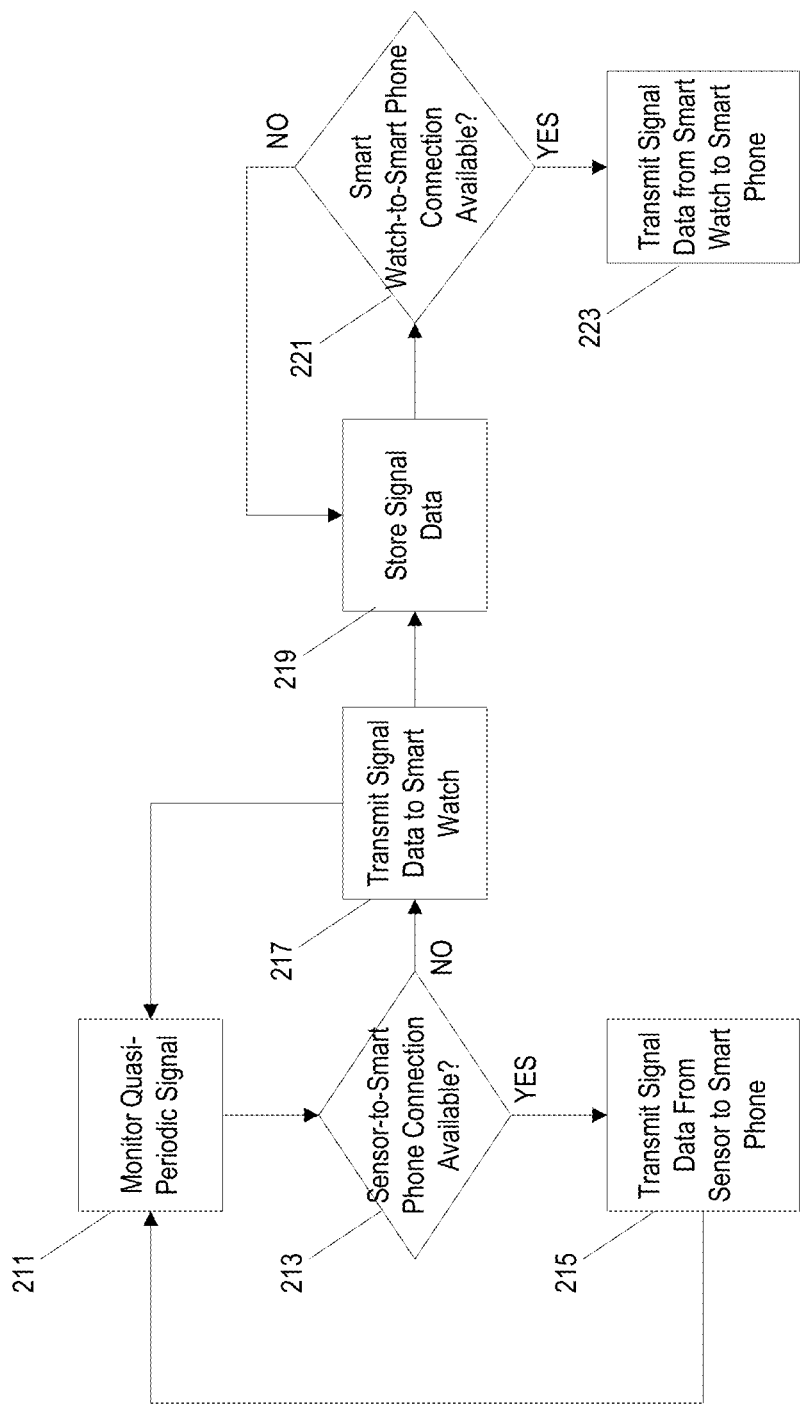
FIG. 2B is a flowchart of a method for facilitating communication in the configuration of FIG. 2A.

FIG. 2B illustrates one example of a method for communicating sensed signal data to the base station using the smart watch as an intermediate communication device. The wearable sensor device 201 monitors a quasi-periodic signal (e.g., an ECG signal of the user) (step 211). The wearable sensor device 201 then determines whether wireless communication between the wearable sensor device 201 and the smart phone 203 is available (step 213). If the sensor-to-smart phone wireless connection (e.g., wireless communication connection "A" in FIG. 2A) is available, then the wearable sensor device 201 transmits the signal data directly to the smart phone 203 (step 215). However, if the sensor-to-smart phone wireless connection is not available, then the ECG sensor device 201 transmits the signal data to the smart watch 207 (step 217). The smart watch 207 stores the received signal data (step 219) and determines whether wireless communication between the smart watch 207 and the smart phone 203 is available (step 221). If the smart watch-to-smart phone connection is available, then the smart watch transmits the signal data to the smart phone (step 223). Otherwise, the smart watch 207 continues to store the signal data until the smart watch-to-smart phone wireless connection can be established or, in some implementations, until the amount of signal data stored on the memory of the smart watch 207 exceeds storage limit.

Systems and methods outlined in this disclosure provide mechanisms for capturing/sensing physiological data and communicating that sensed data to a base station. In some examples, the systems and methods described herein provide a generative-model-based compressive sensing (GenCS) that reaps the synergistic benefits of Compressive Sensing (CS) and Generative Modelling (GeMREM) thereby enabling continuous monitoring and data processing in a wearable sensor/processing environment such as, for example, the system using the Smart Watch illustrated in the example of FIGS. 2A and 2B.

Because the resource limitations of a Smart Watch do not allow long term monitoring, in some implementations the smart watch offloads the data processing to a smart phone. An optimized implementation might balance various requirements including: (1) accuracy of recovery (the data recovered from the sensor at the smartwatch should be at least diagnostically accurate as compared to the un-compressed sensed data), (2) execution time (the data recovery algorithm from compressed data is a computationally complex $l_1$ minimization problem. A thread executing the $l_1$ minimization problem may take more time than the total amount of time for which data was sensed), and (3) energy consumption and battery lifetime (The recovery algorithm thread may consume high power and combined with the execution time it may result in prohibitively high energy consumption. This may lead to reduced lifetime of the smartwatch). These benefit trade-offs are governed by the compression ratio of the GenCS algorithm. As the compression ratio increases, the amount of sensed data decreases resulting in faster execution of the recovery algorithm, reduction in power consumption and increase in battery lifetime. However, it may cause a decrease in accuracy. As discussed further below, the GenCS can be tuned to provide fast and energy efficient data recovery while maintaining the required diagnostic accuracy.

The table of FIG. 3 lists several morphological and temporal parameters that might be used for measuring ECG data reconstruction fidelity. Because the error metric of mean square error may not be a suitable way for determining accuracy of ECG signal reconstruction, the table of FIG. 3 provides a comparison of the parameter error using GeMREM techniques and using CS techniques. As illustrated in this example, the GeMREM technique is more accurate in preserving shape properties of ECG signals (i.e., morphology parameters) while CS is more accurate in recovering temporal properties.

Figure 4:
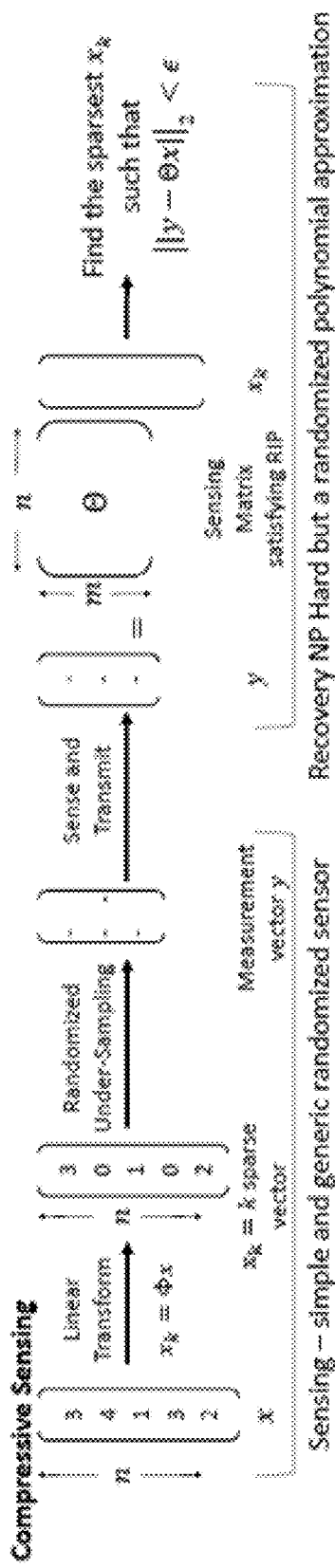
FIG. 4 is a flowchart of a method for monitoring and reconstructing a signal using compressive sensing.

FIG. 4 illustrates a technique for sensing and reconstruction of an ECG signal using compressive sensing (CS). Consider a compressible signal $x \in \mathbb{R}^n$ that has a sparse representation $\alpha \in \mathbb{R}^n$ on a certain orthogonal basis $\Phi \in \mathbb{R}^{n \times m}$ given as $x = \Phi a$, a is a k-sparse vector that contains only k non-zero elements. Given a random sensing matrix $\Theta \in \mathbb{R}^{m \times n}$, the measurement signal $y \in \mathbb{R}^m$ is given by $$y = \Theta x = \Theta \Phi a, \quad (1)$$

As long as the sensing matrix $\Theta$ satisfies the Restricted Isometry Property (RIP) of order 2 k, the signal information a can be well preserved by the random encoding (RE) scheme in Equation 1. This holds true even if the sensing matrix $\Theta$ is an underdetermined matrix (m<n), which represents a dimensionality reduction from $\mathbb{R}^n$ to $\mathbb{R}^m$. Therefore, the random sample is a compressed representation of the signal coefficient a that is encoded by $A = \Theta \Phi$. A sensing matrix randomly generated from Bernoulli distributions can also satisfy the RIP of order 2 k for m=O(k*log (n/k)). Accordingly, the undersampling ratio (m/n) or compression ratio (n/m) achievable by compressive sensing is proportional to the signal sparsity k on the chosen basis Φ.

To recover the sparse coefficient a (original signal x can be then reconstructed as x=Φa), we need to solve the underdetermined linear equation in Equation 1. By utilizing the sparsity condition as prior knowledge, a can be exactly recovered by solving the sparse approximation (SA) problem ($l_0$ pseudo-norm minimization) defined as $$\min_{\alpha} \|\alpha\|_0, \text{ subject to } \|y - \Theta\Phi\alpha\|_2^2 \leq \zeta. \quad (2)$$

where ε is an error tolerance term to enhance the reconstruction robustness considering that the random sample is contaminated by an additive noise. The SA problem is to find the sparsest vector out of the solution space of $|y-\Theta\Phi\alpha\|_2^{2}\vartheta$. Although the SA problem in Equation (2) is NP-hard, its solution can be robustly estimated by either heuristic methods such as orthogonal matching pursuit (OMP) or linear programming through the relaxation to a basis pursuit ($l_1$-norm minimization) problem.

Figure 5:
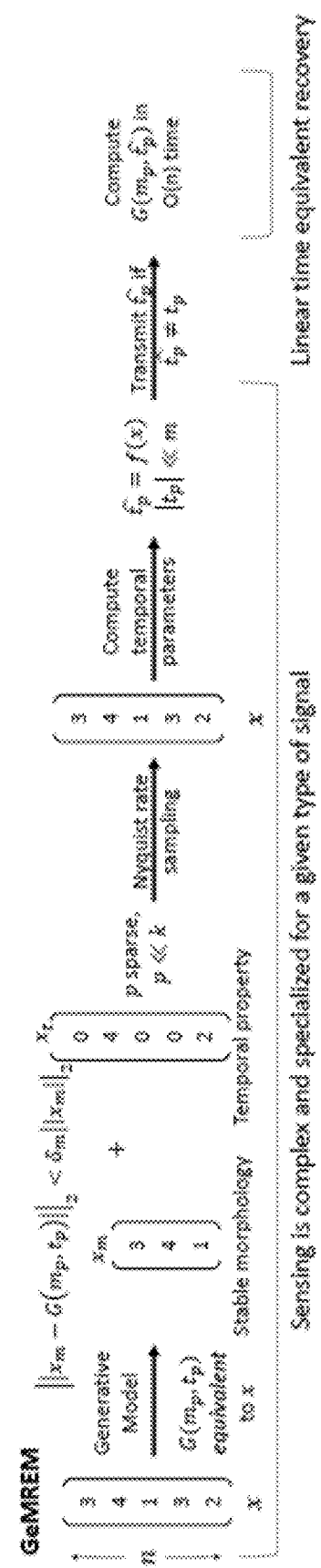
FIG. 5 is a flowchart of a method for monitoring and reconstructing a signal using generative modeling.
Figure 6:
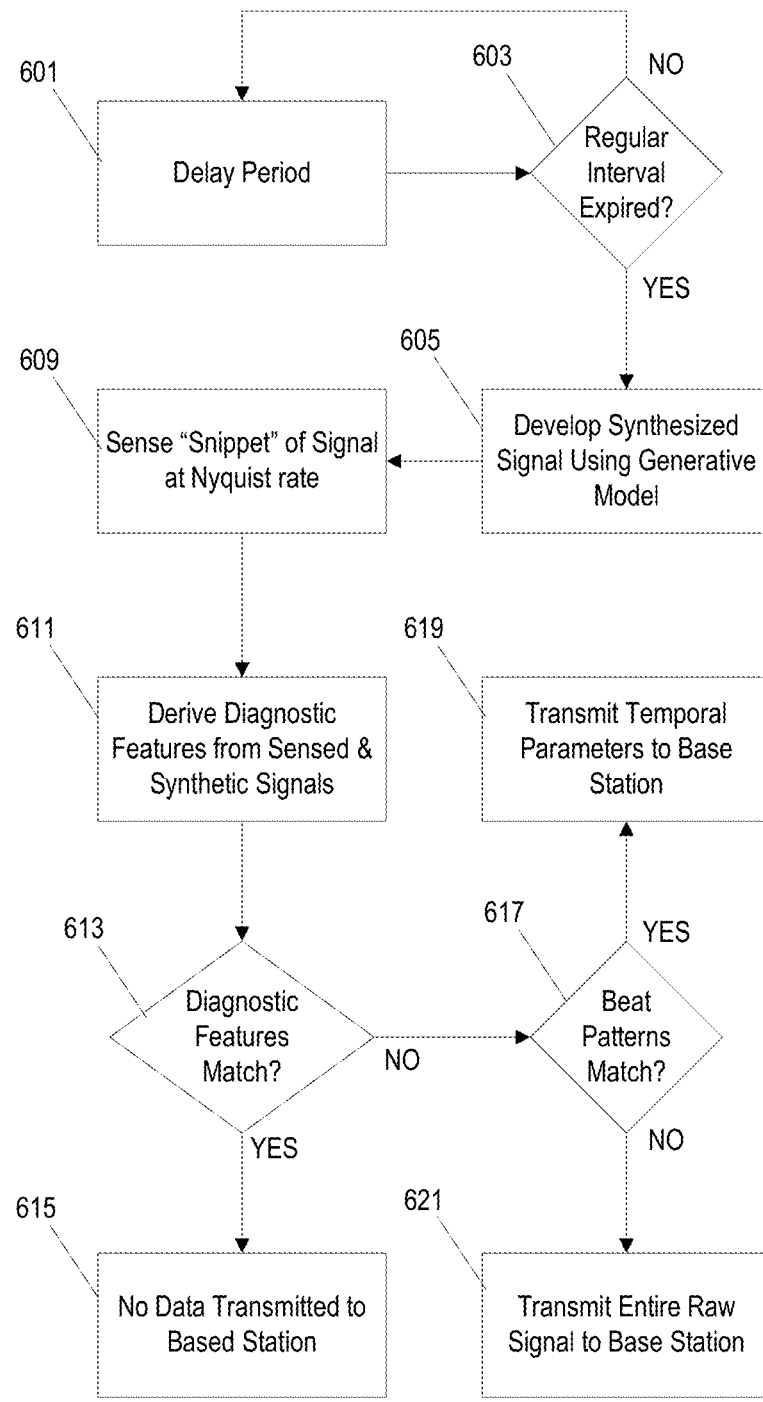
FIG. 6 is a flowchart of a method performed by a sensing device for capturing signal data using the generative modeling technique of FIG. 5 and transmitting data to a base station for reconstruction of the captured signal.
Figure 7:
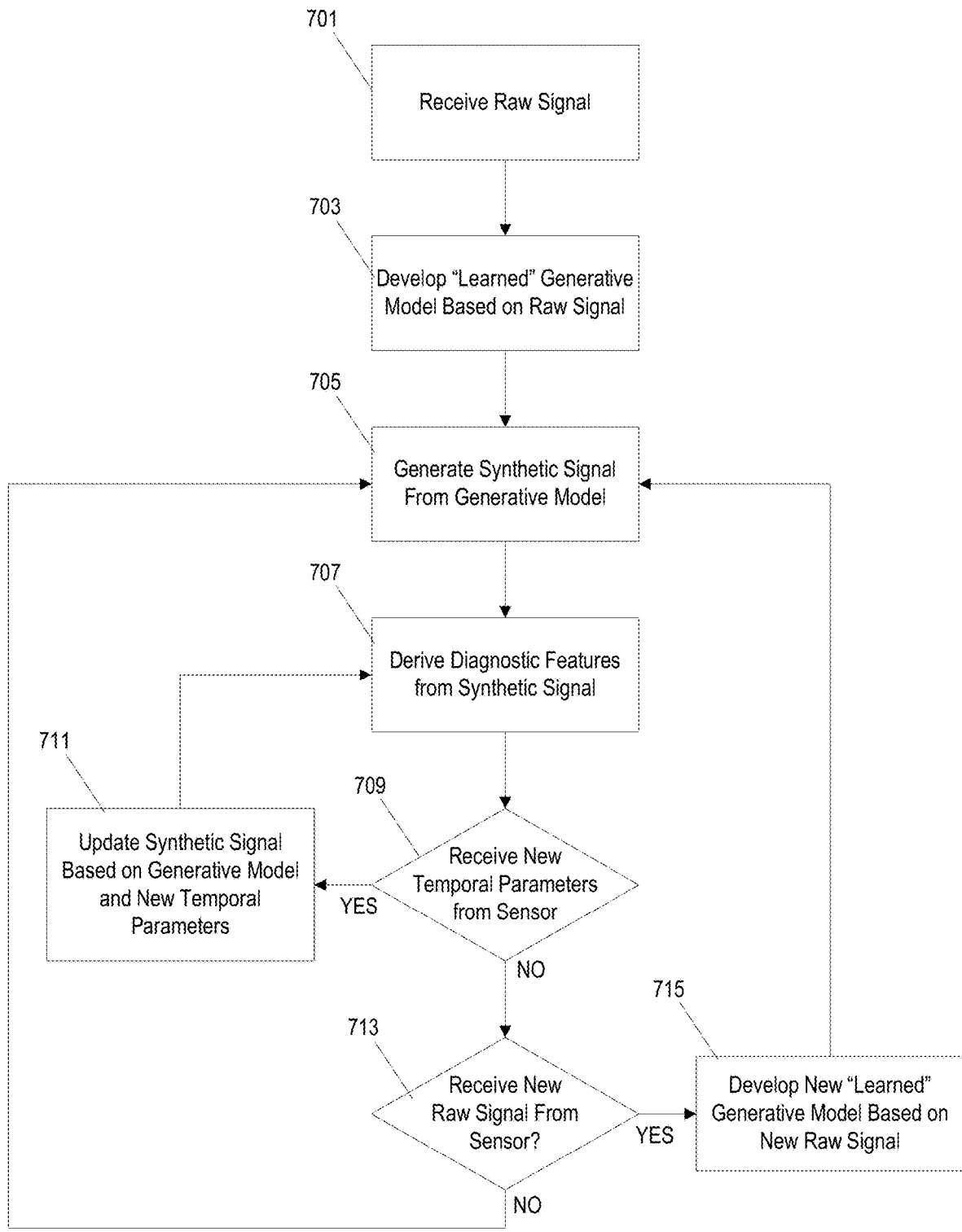
FIG. 7 is a flowchart of a method performed by a base station for reconstructing the signal using the generative modeling technique of FIG. 5 and data received from the sensing device in the method of FIG. 6.

FIG. 5 illustrates the GeMREM sampling and recovery mechanism. FIG. 6 illustrates a method for sensing and transmitting signal data according to GeMREM and FIG. 7 illustrates a method for recovering the signal. In some implementations, the wearable sensor device (e.g., ECG sensor 201) or the intermediate communication device (e.g., smart watch 207) may be configured to perform the method of FIG. 6 to transmit signal data to the base station (e.g., the smart phone 203) and the base station (e.g., the smart phone 203) may be configured to perform the method of FIG. 7 to recover the original sensed signal.

GeMREM works by first learning a generative model G of a shape characteristic of a signal. These generative models if provided with the correct inputs can output a synthetic signal that is equivalent to the original signal with respect to diagnostic features as may be determined by trained physicians. At regular intervals (e.g., upon expiration of a delay period in the example of FIG. 6 (steps 601 and 603), the sensor senses a snippet at Nyquist rate (step 609) and derives diagnostic features from the sensed signal (step 611). The sensor (or the intermediate communication device) also generates a synthesized signal using the learned generative model (step 605) and derives diagnostic features from the synthesized signal (step 611). If the diagnostic features derived from the signal snippet match the stored features of the synthesized signal (step 613) then the sensor does not transmit any data to the base station (step 615). Accordingly, the base station would continue to use the same generative model to regenerate a diagnostically equivalent signal (as discussed further below). However, if the diagnostic feature values do not match (step 613), then the sensor may determine whether to send an entire raw signal to the base station or to only send a smaller "feature update" to the base station to be used to update/tune the generative model that is used by the base station. In the example of FIG. 6, the sensor (or the intermediate communication device) is configured to determine if the beat patterns in the sensed signal "snippet" match the beat patterns from the synthesized signal (step 617). If the beat patterns of the sensed ECG signal and the synthesized ECG signal match, then the sensor transmits an updated set of temporal parameters to the base station (step 619). However, if the beat patterns do not match, then the sensor sends the entire raw signal to the base station (step 621).

FIG. 7 illustrates an example of how the base station may be configured to utilize the generative model of the GeMREM mechanism to recover the signal. First, when the base station receives raw signal data from the sensor or an intermediate communication device (step 701), then the base station develops a "learned" generative model based on the raw signal (step 703). Once the generative model is established, the base station utilizes the generative model to generate a synthetic version of the signal (e.g., a synthetic ECG signal) (step 705) and diagnostic features can be derived from the synthetic signal as may be necessary (step 707). As discussed above in reference to FIG. 6, the sensor (or the intermediate communication device) is configured to transmit either a set of temporal parameters or new raw data from the sensor if the diagnostic features of the sensed signal no longer match the diagnostic features of the synthetic signal. Accordingly, when the base station receives new temporal parameters from the sensor (or from the intermediate communication device) (step 709), the base station updates the synthetic signal based on the generative model and the new temporal parameters (step 711) and continues to derive diagnostic features from the updated synthetic signal (step 707). However, if the base station receives new raw signal data from the sensor (step 713), then the base station develops a new "learned" generative model based on the new raw signal data (step 715).

Using a generative model (such as the ECGSYN model), for the morphology features, each wave (P, Q, R, S, and T) is represented by 3 parameters: (a, b, θ), which determine its height and distance to R peak, respectively. A single beat of ECG signal is thus given as $$\hat{z}(t) = -\sum_{i \in \{P,Q,R,S,T\}} a_i \Delta\theta_i \exp(-\Delta\theta^2 / 2b_i^2), \quad (3)$$

The parameter $\Delta\theta_R=0$, while $\Delta\theta_i$ is given by the scaled temporal difference between the i peak and the R peak. For a given patient, the parameters $a_i$, $b_i$, and $\theta_i$ have to be learned. In some implementations, a two minute sample of the raw ECG signal is used to learn these parameters.

As illustrated in FIG. 4, the CS theory argues that a k-sparse n-dimensional signal can be accurately recovered with m<<n samples collected using a m×n sensing matrix Θ instead of an n×n identity matrix, where n is the Nyquist mandated number of samples. When the measurement vector for the sensor y=Θx has much fewer samples m than n, the sensor that uses CS is much simpler than a sensor sensing at Nyquist rate. This leads to significant improvements in power consumption, form factor, and storage capacity. Since the original signal x is k-sparse, the measurement signal y is basically a linear combination of at most k non-zero elements of x. If the position of the k non-zero elements were known, then finding the sensing matrix and then subsequently recovering x would be relatively straightforward as discussed in reference to FIG. 4 above. However, since the positions are not known, every possible m×k submatrices of Θ must be searched to find the best k sparse approximation of x. This problem is an NP hard and has combinatorial complexity. However, with random sampling, it can be solved in polynomial time. Compressive sensing thus allows us to recover relevant information from signals using simpler sensors, by exploiting the sparsity of signals in linear domain, and solving an NP hard recovery problem in polynomial time by using randomized sampling.

In many practical scenarios, signals may not be sparse or even compressible (i.e., approximated using a sparse signal) in any linear transformed domain. Such signals often have a unique shape property that is repeated at random intervals. These signals are referred to herein as quasi-periodic signals. For example, signals from the human body such as electrocardiogram (ECG), or brain signals, or chaotic signals are not sufficiently sparse in any linear transform domain for CS to be beneficial. The complex shape characteristics of these signals can be modeled using non-linear generative models. The models encode significant information from the raw data, which are used for decision making. As such for many applications the raw data is less significant than these models. Further, in many practical applications, two data sets or signals with high sample-by-sample error may contain the same relevant information, and are equivalent. Hence, a generative model is a nonlinear sparsifying operator, which sparsifies a signal with respect to relevant information content. This is typically true in cases of physiological sensing, where the diagnosis of a disease is performed based on ranges of metrics derived from the signal and not the exact signal value. Two signals differing sample-by-sample may not be diagnostically different. Thus, instead of recovering with the goal of sample-by-sample accuracy, it may be sufficient to recover an equivalent signal that has the same relevant information as the original signal sampled at Nyquist rate.

With this observation in-the-field, the Generative Model based Resource Efficient Modeling (GeMREM), which (as illustrated in FIG. 5) considers that the relevant information in a quasi-periodic signal x can be encoded in a generative model $G(m_p; t_p)$ having two parameters: a) morphology $m_p$, which characterizes the unique shape property of the signal and b) temporal properties $t_p$, which characterizes the underlying temporal variations. The generative model provides a signal that is equivalent to x with respect to certain relevant information. Further, $m_p$ is relatively stable and does not change over time. As discussed above in reference to FIG. 6, a sensor samples the signal x at Nyquist rate and compares it with a generative model. Thus, the sensor device (or the intermediate communication device) for GeMREM is much more complex than a sensor device simply sensing at Nyquist rate or executing CS as it must be able to calculate a synthesized signal. The sensor device then transmits only the changes in $t_p$ to the recovery algorithm. Using $t_p$ and previously learned $m_p$ the equivalent signal $G(m_p; t_p)$ can be recovered in linear time, O(n). With such non-linear sparsifying operators and the idea of equivalent reconstruction, GeMREM was found to achieve 40 and 300 times communication compression for ECG and photoplethysmogram signals, respectively. Such compressions are much greater than the in-the-field sensing compression performance of CS algorithms.

In summary, CS exploits sparsity in linear domain, reduces sensing frequency, and recovers randomly under-sampled signals by minimizing sample by sample error. Although the sensor device is very simple and has significant sensing power savings, the recovery is complex, and the data compression ratio is much less than GeMREM. On the other hand, GeMREM exploits unique shape properties of signals by representing them using nonlinear sparsifying operators with morphology and temporal parameters, and uses the paradigm of equivalent reconstruction to reduce data communication frequency. GeMREM sensors are more complex and tuned to a specific type of signal, however, in-the-field GeMREM provides orders of magnitude more compression ratio than CS.

Figure 8:
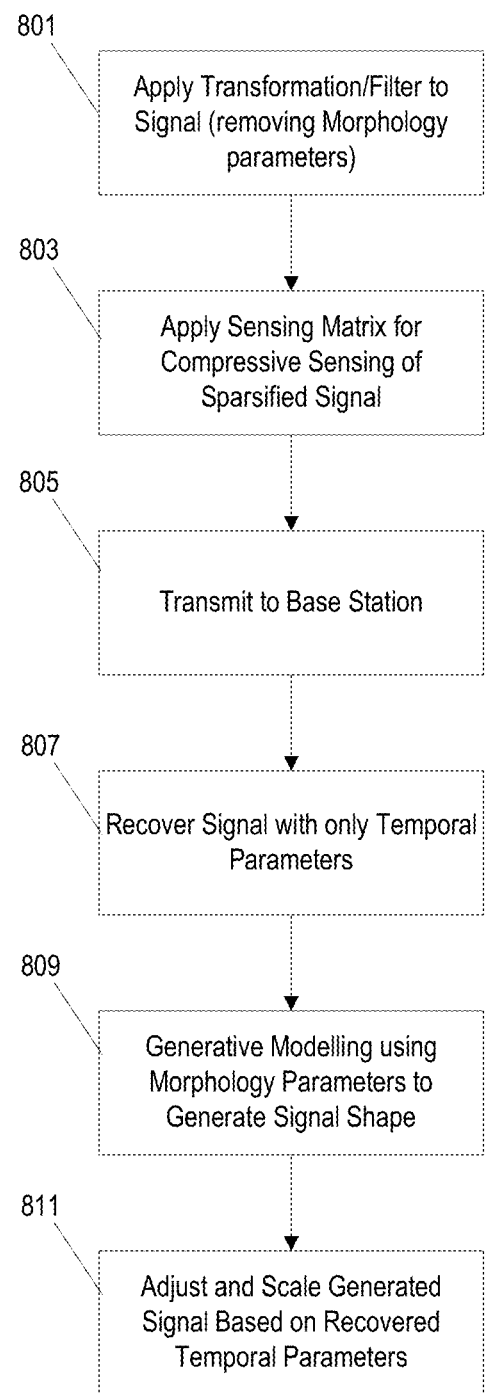
FIG. 8 is a flowchart of a method for capturing and reconstructing a signal using Generative Model-Based Compressive Sensing (GenCS).

FIG. 8 illustrates another mechanism (referred to herein as GenCS) that achieves the sensor device processing simplicity of CS, the compression ratio of GeMREM, and recovers signals that are equivalent in features relevant to the application (e.g., a diagnostically equivalent signal). First, a transformation/filter is applied to a sensed signal (step 801). This transformation/filter sparsifies the signal and removes morphology parameters while leaving temporal parameters in the sparsified signal. A sensing matrix is then applied for compressive sensing of the sparsified signal (step 803). The sampled sparsified signal is then transmitted to the base station (step 805) where the sparsified signal with only temporal parameters is recovered (step 807). Generative modelling is then used to generate a signal shape with morphology parameters (step 809). The signal shape that is reconstructed with the morphology parameters is then further adjusted and scaled based on recovered temporal parameters from the sampled sparsified signal received by the base station in order to generate a recovered signal (step 811).

As discussed above, a shape preserving generative model requires morphological $m_p$ and temporal parameters $t_p$ from the quasi periodic signal x. The algorithms used for computing $m_p$ and $t_p$ is highly non-linear and includes functions such as peak detection and curve fitting optimizations. Since x is quasi-periodic, then there exists a sub sequence $x_m$ of x such that $x_m$ has the unique shape property that is repeated at random periods. If $G(m_p; t_p)$ is the generative model of the signal x, then according to definition of a generative model we have $$\|x_m - G(m_p, t_p)\|_2 \leq \delta_m \|x_m\|_2, \quad (4)$$

where $\delta_m$ is the morphology tolerance level of the model.

The morphological properties of the signal x can be suppressed to derive a signal $x_t$, which has only the temporal properties of x, i.e., $f(x_t) = f(x)$. This can be done using digital filters that suppress certain frequencies that are affected by the specific shape criteria. Such filters can be realized as a linear transformation on x, $x_t = Dx$. For the generative model, the temporal parameter is again within certain tolerance bound of the parameters derived from x as shown in Equation 5.

$$\|f(x_t) - f(G(m_p, t_p))\|_2 \leq \delta_t \|f(x_t)\|_2, \quad (5)$$

Note that if x is k-sparse, then $x_t$ is p-sparse, where p<<k. This is because in $x_t$ is obtained by suppressing the morphological properties in x. Hence the process of extracting the temporal parameters from $x_t$ is a non-linear sparsifying operation. We can now define a generative model $G(m_p, t_p)$ as equivalent to the signal x if it satisfies Equations (4) and (5).

We attempt to derive approximate morphological and temporal parameters $\{\tilde{m}_p, \tilde{t}_p\}$ from the randomly sampled time series y, such that $G(\tilde{m}_p; \tilde{t}_p)$ is equivalent to x. In order to have such a mechanism, we need a sensing matrix that satisfies the Restricted Isometry Property (RIP) for the generative model $G(m_p; t_p)$. Since x is a k-sparse signal, then there exists a sensing matrix $\Theta$ that satisfies RIP for x for some conditioning parameter $\varepsilon$.

If x is k-sparse, then there exists $\Theta \in \mathbb{R}^m \times \mathbb{R}^n$, for $m = O(k * \log(n/k))$ such that $$(1-\varepsilon)\|x\|_2 \leq \|\Theta x\|_2 \leq (1+\varepsilon)\|x\|_2 \quad (6)$$

By combining Equations (6) and (4) and doing some algebraic manipulations, we get $$(1-\varepsilon-\delta\|\Theta\|_2)\|x\|_2 \leq \|\Theta G(m_p, t_p)\|_2 \leq (1+\varepsilon+\delta\|\Theta\|_2)\|x\|_2 \quad (7)$$

Hence Θ satisfies RIP of order at least 2 k for $G(m_p, t_p)$ with $\varepsilon'=\varepsilon+\delta\|\Theta\|_2$.

Thus, the generative model $G(m_p; t_p)$ provides at least k-sparsity in a signal x. Note that generative model has a higher value of conditioning parameter. This means that it classifies a larger neighborhood of x as equivalent. Hence, it provides more sparsity.

With respect to the temporal parameters, there exists a sensing matrix $\Theta' \in \mathbb{R}^s \times \mathbb{R}^n$, s<m, that can be used to recover a signal with a temporal property equivalent to that of x. Let us consider a recovery algorithm Δ that solves the problem in Equation (2). Hence $\|x-\Delta(\Theta x)\|_2 \leq \zeta$, where $\zeta>0$ is a small number. Hence, $\|f(x)-f(\Delta(\Theta x))\|_2 \leq \delta_t\|x\|_2$. Let us consider that there exists a digital filter D such that $x_t=Dx$ and $f(x_t)=f(x)$. Thus, using the same Θ we can recover $x_t$ from m samples. Note that $x_t$ is much sparser than x. There exists $\Theta' \in \mathbb{R}^s \times \mathbb{R}^n$, s<m, such that $\|x_t-\Delta(\Theta' x_t)\|_2 \leq \zeta$. Thus, using just s samples one can recover the temporal properties of x.

The discussion above demonstrates that the temporal property extractor along with the equivalence condition is also a non-linear sparsifying operation. Given a matrix with RIP property for the generative model and a temporal parameter estimation mechanisms as described above, the following problem formulation must have a feasible solution:

$$\text{find } \tilde{m}_p, \tilde{t}_p \text{ to minimize } \|G(\tilde{m}_p, \tilde{t}_p)\|_1$$

$$\text{such that } -y=\Theta G(\tilde{m}_p, \tilde{t}_p) \quad (8)$$

A solution to this problem provides the recovery of a diagnostically equivalent signal.

The shape of a beat makes an ECG signal a non-sparse signal not only in time domain but also in DWT, DFT, and DCT domains. However, the temporal parameters are only related to the R peaks. Hence a signal with only R peaks can be approximated much more accurately using greater sparsity. The GenCS method of FIG. 8 senses the signal to only recover the temporal parameters (R peaks for ECG) and suppress the morphological parameters. The morphological parameters can be learned from a signal snippet sensed at the Nyquivst rate. On obtaining the temporal parameters, the entire signal can be recovered by combining the morphological and temporal parameters.

For ECG signals the shape characteristics can be suppressed using a low pass and high pass filter combination. A digital filter defined by the Equation $$y[i]=2y[i-1]-y[i-2]+x[i]-2x[i-6]+x[i-12],$$

$$z[i]=32x[i-16]-z[i-1]+x[i]-x[i-32], \quad (9)$$

at low pass cut-off frequency of 5 Hz and high pass cutoff at 12 Hz, can effectively eliminate the P, Q, S, and T waves, and only keep the R peaks in the signal. The resulting signal z has only the temporal parameters and the morphology is suppressed. The signal z is compressible to a sparse vector and can be recovered with very less number of samples.

A sensing matrix Θ is generated using a Bernoulli distribution and a transformation matrix Θ for making the original signal sparse was obtained by first converting the band-stop filter in Equation 9 into a matrix form and multiplying it with the DWT matrix. These matrices are applied to sample an ECG signal and to capture temporal parameter data. This sampled data is transmitted to a base station and the Homotopy recovery algorithm was used to recover the signal with only temporal parameters. A reconstructed signal is generated using the morphological parameters of the signal that were learned previously using a curve fitting technique. The ECG beat shape of the reconstructed signal is then centered at each R peak obtained from the recovered temporal parameter signal and temporally scaled to match the heart rate and to provide a diagnostically equivalent reconstructed signal.

Figure 9:
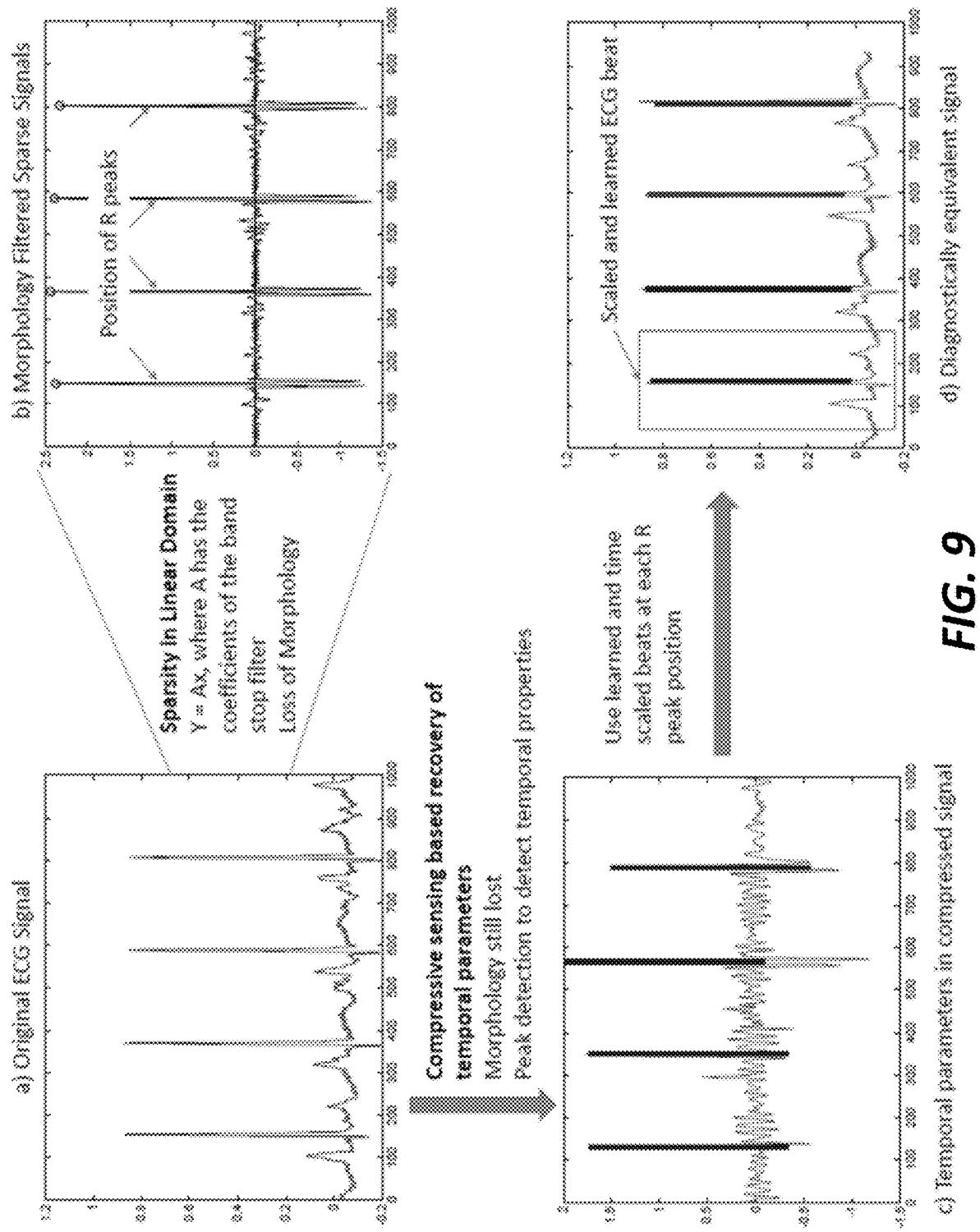
FIG. 9 is a series of graph illustrating (A) a raw ECG signal, (B) the ECG signal filtered to remove morphology parameters, (C) the temporal parameters of the ECG signal captured using the GenCS method of FIG. 8, and (D) a diagnostically equivalent ECG signal reconstructed using the method of FIG. 8.

FIG. 9 graphically illustrated the GenCS mechanism for signal reconstruction. Graph (a) shows an original raw ECG signal including both the temporal and morphology parameter components. Graph (b) shows the signal of Graph (a) filtered to remove the morphology components. Graph (c) illustrates the recovered sparsified signal generated by the base station by applying the homotopy recovery algorithm to the sampled temporal data. Graph (d) shows the reconstructed signal generated by the base station by adjusting and scaling the previously learned morphology data based on the recovered temporal data of Graph (c). The reconstructed signal of Graph (d) is diagnostically equivalent to the original raw ECG signal of Graph (a).

Returning now to the example of FIGS. 2A and 2B, in some implementations, the system may be configured to use a different sampling/compression mechanism depending on which communication link is established. For example, in some implementations, the wearable sensor device may be configured to send raw signal data to the base station if it is able to establish wireless communication directly between the wearable sensor device and the base station (e.g., wireless communication connection "A") and to use the GenCS method described to transmit signal data to the intermediate communication device if direct wireless communication to the base station cannot be established.

Furthermore, returning now to the example of FIG. 1, a wearable sensor device that is implemented, for example, as a smart watch or a belt pack may be configured to receive raw signal data from a sensor (or a combination of sensors) through either wired or wireless communication and then transmit the signal data to the base station using the GenCS method. Accordingly, in one example, a smart watch (operating as the wearable sensor device) may be configured to receive raw or compressed ECG signal data from an ECG sensor and to then transmit the ECG signal data to a smart phone (operating as the base station) using the GenCS method.

FIGS. 10-15 illustrate a clinical study performed to evaluate the GenCS signal recovery method described above. Twenty five patients from an ICU volunteered to participate in the study—fourteen of them were men and eleven were women. One of the patients had frequent atrial fibrillation which was captured by GeMREM through raw data transmission. The age of the patients were not recorded. The patients had limited mobility and the study devices were un-installed when the patients went for procedures such as MRI.

Subjects were monitored for a period of approximate 20 hours using a Shimmer device and Holter monitor as illustrated in FIG. 10. The Shimmer device 1001 is a small and lightweight (28 g) plastic box equipped with a MSP-430 microcontroller and a lithium ion battery. The Shimmer device 1001 was worn by the patient using a chest strap. The Shimmer device 1001 communicated with a Google Nexus One Android phone 1003 through a Bluetooth connection. In addition to the study device, a standard 5 lead Holter monitor 1005 was also used to collect ECG signals on a sample by sample basis.

Three Ag—Cl electrodes were placed on the chest of the patient in the form of a triangle to measure ECG using Shimmer sensors as shown in FIG. 10. A ground lead was also placed near the abdomen and away from the triangle formed by the other three leads. To ensure that the spatial distance between the electrodes of the Shimmer sensor and the standard monitor are not significant, we used CardiacDirect double leads, which have two solid gel electrodes placed at a distance of 2 in from each other. On the double electrodes, a lead of the standard monitor and a Shimmer lead were attached. This ensured that the measurement artifacts due to separation of lead are minimized. These leads were connected to a Shimmer device 1001 which was worn by the patient using a chest strap. The GeM-REM protocol was started and each update from the sensor was time stamped to ensure synchronization between the standard monitor 1005 and the Shimmer device 1001. The monitoring was continued for at least 16 hours and maximum up to 24 hrs.

Prior to deploying the system for a patient, the learning functionality is used to train the generative model using the patient's ECG data. This training process outputs a set of parameter values which are stored on the base station as well as the sensor. These values are intended to be used as inputs for generating synthetic ECG data closely resembling the patient's actual ECG. Thus, data collection was performed in two steps: a) initially a 2 minute sample of ECG is obtained using the Shimmer sensor for training a personalized generative model, and b) the new generative models were manually entered to the Shimmer sensor and then data for 24 hours was collected.

In addition to the 25 testing subject from the ICU, data from twelve preterm infants was also analyzed. The preterms had a gestational age of <36 weeks and postconceptional age of >30 weeks at the time of study and spontaneously breathing room air or receiving supplemental $O_2$ through nasal cannulae at a fixed flow rate. Overall, we tested the GenCS and CS techniques on 37 subjects.

The GenCS and CS techniques were evaluated on two sets of accuracy metrics: a) error in temporal parameter with respect to data from Holter monitor 1005, which include mean heart rate, standard deviation of heart rate, and low frequency to high frequency ratio of heart rate variation, and b) error in morphological features with respect to Holter monitor 1005. In the analysis we have divided the entire 24 hour signal into intervals of 1000 samples. For each such interval, we compute the temporal and morphological features and then compare the average error of GenCS and CS with respect to Holter monitor data over all such intervals.

The performance of the signal recovery algorithm was also evaluated based on execution time and energy consumption on a smartphone and a smartwatch. The lifetime difference of the device when it executes the cardiac monitoring system with GenCS was also evaluated in comparison to a cardiac monitoring system with CS.

We implemented the GenCS and CS in a Nexus 5 Android smartphone running the Kitkat OS version API 19. We also implemented both in an android smartwatch ZGPAX, which also ran the same version of Android OS API 19. To isolate energy consumption of the recovery algorithm, we implemented a simple UI, we stored a data snippet of 1000 samples (2 s) and also stored the sensing matrix. The test app only had the execution of a Homotopy algorithm. We compiled the Homotopy algorithm implementation in a jar file and included it in the test app source code. The execution time was measured using the system time service of android. The power consumption in the smartphone was measured using the PowerTutor application. However, the smartwatch was not supported by PowerTutor. Hence, for the smartwatch we ran the test app for 3 hours and measured the difference in state of charge.

Figure 11:
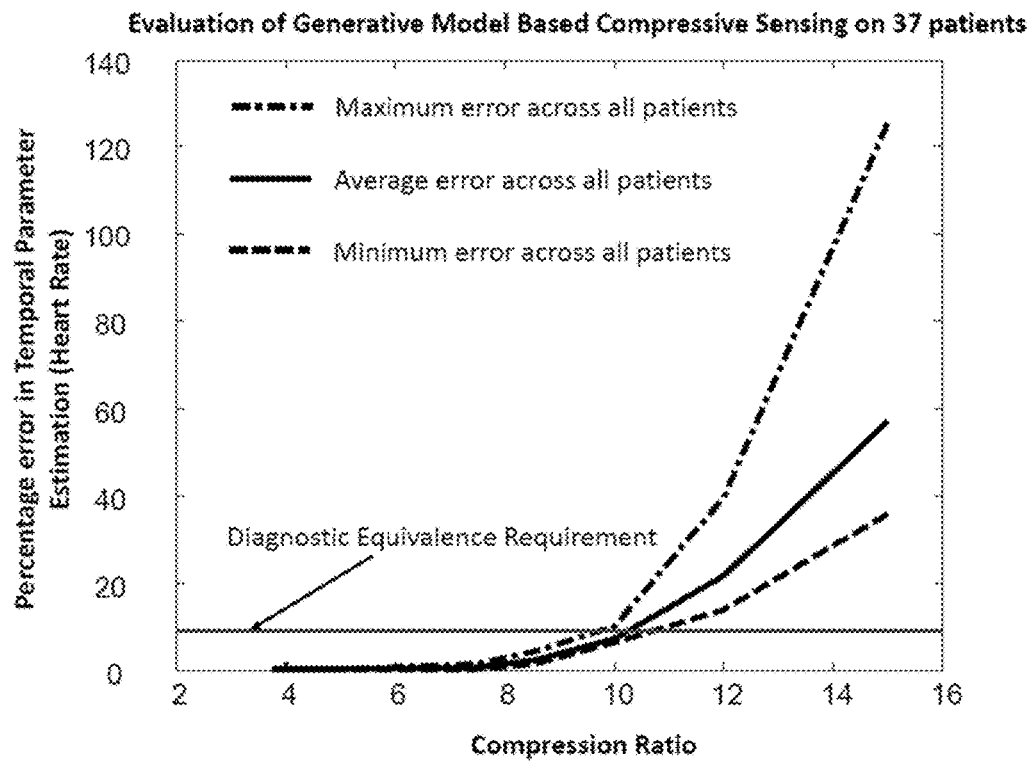
FIG. 11 is a graph of temporal parameter estimation error with respect of compression ratio using the GenCS method of FIG. 8.

The compression ratio for the ECG data based on GenCS is shown in FIG. 11. It shows that the error in estimation of R-R intervals increases with increase in compression ratio. However, if we only care for diagnostic accuracy, then an error of 10% can be tolerated. For such a tolerance we obtain a compression ratio of around 10. This is significantly higher than the traditional compressive sensing techniques which could on an average achieve a compression ratio of 2. This five time increase in compression ratio is attributed to two factors: a) the removal of shape features using a linear filter, and b) the requirement of diagnostic equivalence.

With respect to the shape parameters, GenCS has the same accuracy as GeMREM, however, CS has lower shape accuracy than GenCS as shown in the table of FIG. 12.

Figure 13:
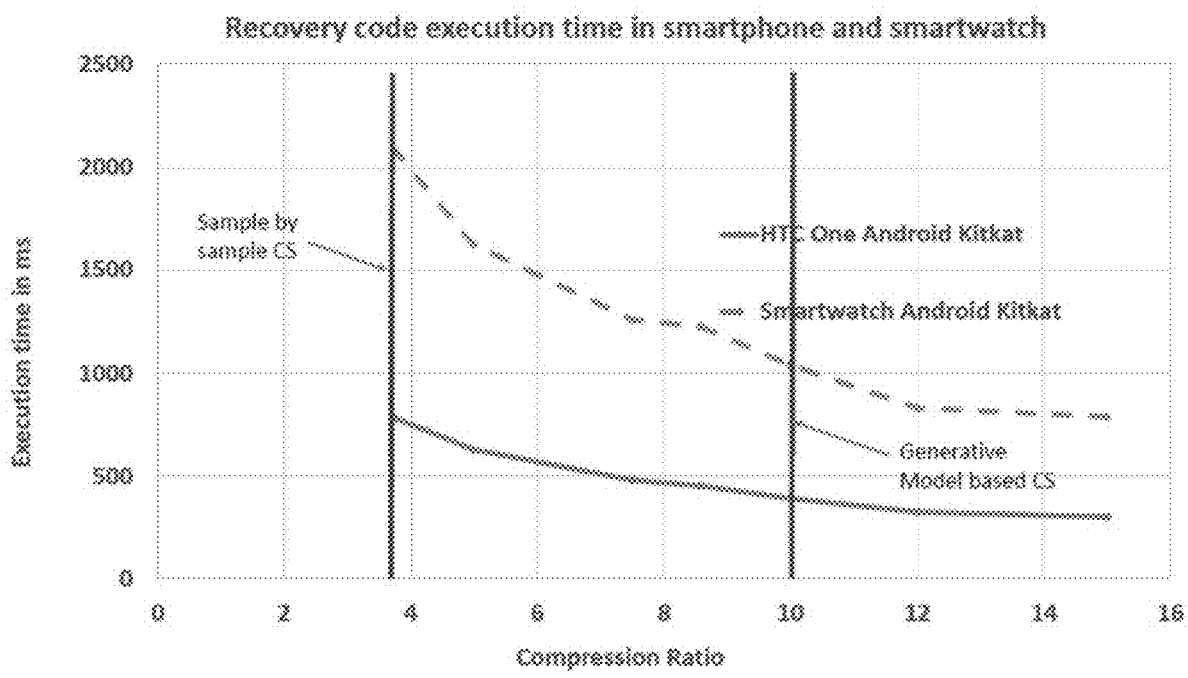
FIG. 13 is a graph of execution time of the recovery algorithm for a smart-watch and a smart-phone with respect to compression ratio.

The execution time of the recovery algorithm decreases non-linearly with the increase in compression ratio as seen in the graph of FIG. 13. The smartwatch is around 2.7 times slower than the smartphone. In order to recover 2 seconds of data using CS with a compression ratio of around 2, the smartwatch takes around 2.3 seconds while the smartphone takes around 780 ms. The recovery and sensing is performed by two separate threads with a bounded buffer that stores the sensed data. The sensing thread fills up the buffer, while the recovery thread computes the Homotopy algorithm on the data. For the smartwatch with a limited buffer the CS will cause an overflow of the buffer resulting in loss of sensing data. Hence, the smartwatch can only be used for a limited time to recover data. The smartwatch has to offload the recovery of the data to the smartphone. On the other hand, for the GenCS recovery algorithm, the smartphone takes around 1.1 s to recover 2 s data. Hence, there will be no overflow of the bounded buffer. Hence, the GenCS allows recovery to be performed in the smartwatch itself and does not require offloading to a smartphone. This is especially useful in a free living scenario, where a watch is more easily kept in proximity to a sensor than a smartphone.

Figure 14:
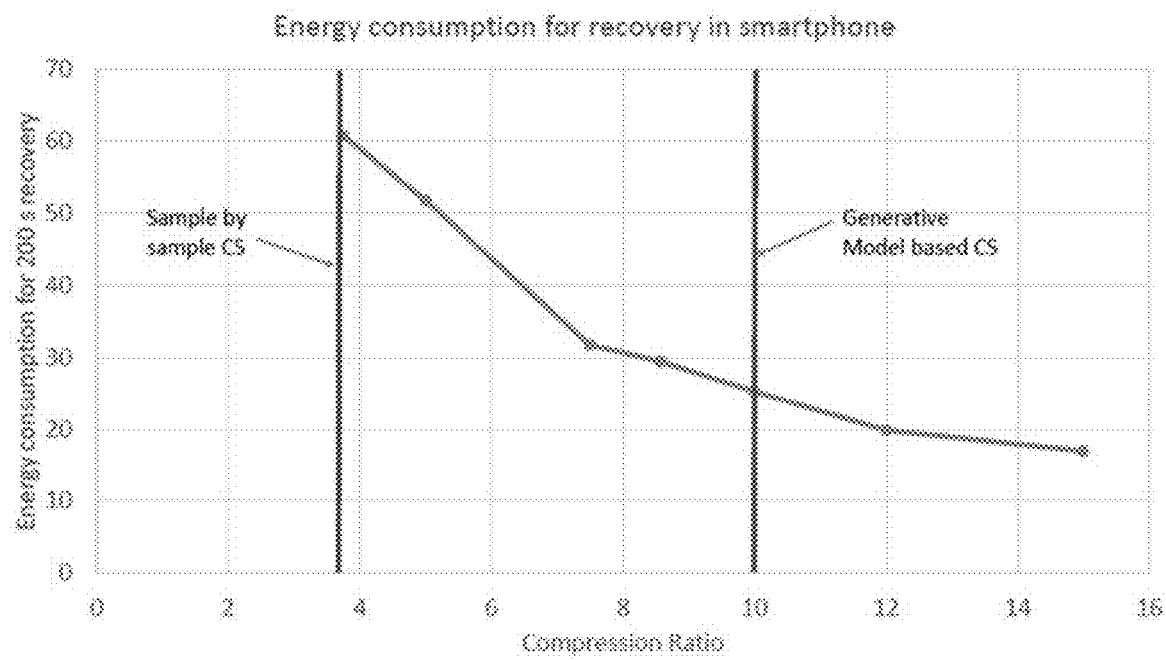
FIG. 14 is a graph of energy consumption of compressive sensing recovery algorithms in a smartphone.

FIG. 14 shows the energy consumption of the smartphone for different compression ratios. As the compression ratio increases the energy consumption decreases. This is because the Homotopy algorithm manipulates a smaller sensing matrix. When the recovery algorithm was executed in the smartphone, it only consumed 36% of the total power consumed by all the apps. To compute the lifetime of smartphone due to the execution of the recovery algorithm, we consider that there are no other apps running. Hence, the whole battery with a capacity of 1625 mAh is utilized by the recovery algorithm.

Figure 15:
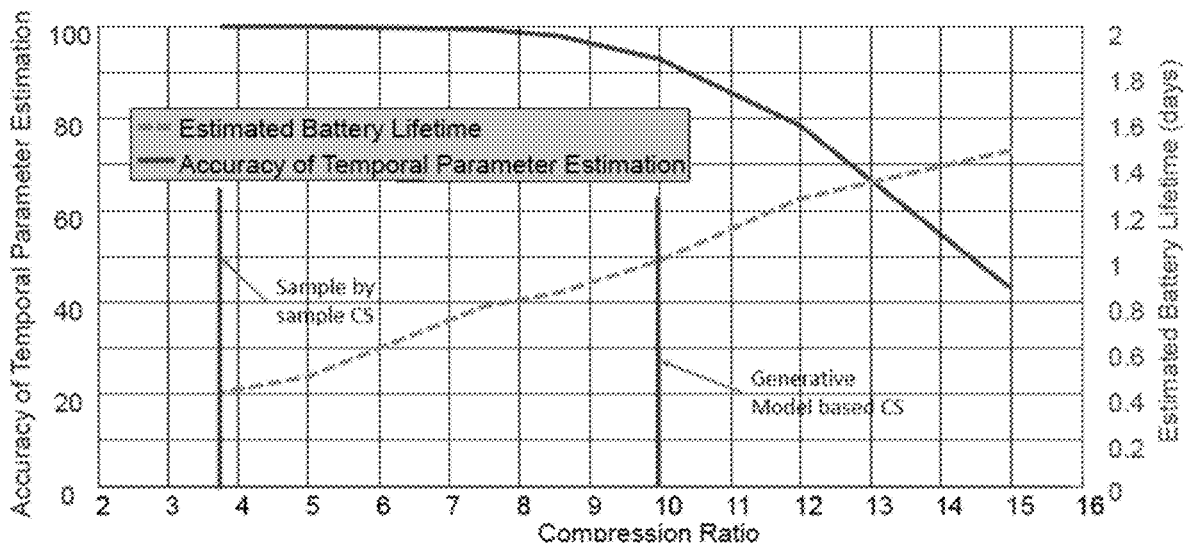
FIG. 15 is a graph of accuracy and lifetime comparison for generative model based CS and sample-by-sample CS.

FIG. 15 shows the lifetime assuming a linear co-relation between energy consumption and battery discharge rate. The lifetime is shown with respect to compression ratio of the CS techniques. In the same graph, we also show the accuracy of extraction of temporal parameters. FIG. 15 shows that as compression ratio increases, the lifetime also increases however, the accuracy decreases. For the GenCS technique, the energy consumption is nearly three times lower than the CS recovery algorithm. The smartphone lifetime for the GenCS for a diagnostic accuracy of 10% is around 1 day which is nearly 15 hrs more than the lifetime of the CS.

Thus, the invention provides, among other things, a system and method for using generative-model-based compressive sensing (GenCS) to capture and recover quasi-periodic signals. GenCS is a significant improvement over CS and combines the shape preserving property and recovery efficiency of GeMREM. GenCS reaps the synergistic benefits of GeMREM and CS and provides a solution that is executable in a smartwatch or smartphone for the long term. GenCS optimizes accuracy and battery lifetime of the smartwatch or smartphone and can operated 3 times longer than CS without the need for battery recharge. This technology makes free living continuous cardiac monitoring a feasible and resource efficient program. Various features and advantages of the invention are set forth in the following claims.

What is claimed is:

1. A monitoring system comprising a wearable sensor device, the wearable sensor device including
   a sensor configured to detect a quasi-periodic signal;
   a wireless transmitter; and
   an electronic processor, the electronic processor configured to
      apply a transformation to generate a sparsified signal based on the quasiperiodic signal, wherein the sparsified signal includes temporal parameters of the quasi-periodic signal and omits all morphology parameters of the quasi-periodic signal,
      sample the sparsified signal, and
      transmit the sampled sparsified signal through the wireless transmitter to a base station device configured to recover the quasi-periodic signal based on the sampled sparsified signal.

2. The monitoring system of claim 1, wherein the sensor includes an ECG sensor, and wherein the quasi-periodic signal includes an ECG signal.

3. The monitoring system of claim 1, further comprising the base station, wherein the base station is configured to
   receive the sampled sparsified signal,
   recover the temporal parameters of the quasi-periodic signal from the sampled sparsified signal,
   generate a reconstructed signal shape using previously captured morphology parameters, and
   generate a reconstructed signal by adjusting and scaling the reconstructed signal shape based on the recovered temporal parameters.

4. The monitoring system of claim 3, wherein the reconstructed signal is diagnostically equivalent to the quasi-periodic signal.

5. The monitoring system of claim 3, wherein the electronic processor of wearable sensor device is further configured to
   determine a sampling rate based on the quasi-periodic signal that will enable the base station to generate the reconstructed signal that is diagnostically equivalent to the quasi-periodic signal, and
   sample the sparsified signal by sampling the sparsified signal at the determined sampling rate.

6. The monitoring system of claim 3, wherein the quasi-periodic signal is an ECG signal, wherein the electronic processor of the wearable sensor device is configured to apply the transformation to generate a sparsified signal by applying a transformation to filter all portions of the ECG signal and leave only R-peaks
   wherein the base station is configured to recover the temporal parameters of the quasiperiodic signal by
      recovering the sparsified signal from the sampled sparsified signal, and
      determining a frequency of R-peaks in the ECG signal from the recovered sparsified signal, and
   wherein the base station is configured to generate the reconstructed signal by adjusting and scaling a previously stored ECG signal shape based on the determined frequency of the R-peaks in the recovered sparsified signal.

7. The monitoring system of claim 1, wherein the electronic processor of the wearable sensor device is further configured to determine whether a wireless communication connection can be established directly between the wearable sensor device and the base station, and
   wherein the electronic processor of the wearable sensor device is configured to apply the transformation to generate the sparsified signal, sample the sparsified signal, and transmit the sampled sparsified signal to an intermediate communication device in response to determining that the wireless communication connection cannot be established directly between the wearable sensor device and the base station.

8. The monitoring system of claim 7, wherein the electronic processor of the wearable sensor device is further configured to:
   establish the wireless communication connection directly between the wearable sensor device and the base station in response to determining that the wireless communication connection can be established, and
   transmitting a signal indicative of the quasi-periodic signal directly to the base station through wireless communication connection when the wireless communication connection is established.

9. The monitoring system of claim 8, wherein the signal indicative of the quasi-periodic signal includes the sampled sparsified signal.

10. The monitoring system of claim 1, further comprising an intermediate communication device,
    wherein the electronic processor of the wearable sensor device is configured to transmit the sampled sparsified signal to the base station device by transmitting the sampled sparsified signal to the intermediate communication device,
    wherein the intermediate communication device is configured to receive the sampled sparsified signal from the wearable sensor device and transmit the received sampled sparsified signal to the base station.

11. The monitoring system of claim 10, wherein the intermediate communication device includes a smart watch and wherein the base station includes a smart phone.

12. The monitoring system of claim 10, wherein the intermediate communication device is further configured to
    store the received sampled sparsified signal to a memory of the intermediate communication device,
    establish a wireless communication connection with the base station, and
    transmit the sampled sparsified signal stored to the memory of the intermediate communication device to the base station after establishing the wireless communication connection with the base station.

13. The monitoring system of claim 1, wherein the wearable sensor device includes a smart watch, wherein the sensor of the wearable sensor device includes a separate wearable sensor, wherein the electronic processor of the wearable sensor device is configured to wirelessly receive the quasi-periodic signal from the separate wearable sensor.

14. The monitoring system of claim 1, wherein the electronic processor of the wearable sensor device is further configured to determine whether a wireless communication connection can be established directly between the wearable sensor device and the base station, and wherein the electronic processor of the wearable sensor device is configured to transmit the sampled sparsified signal to the base station device by
    storing the sampled sparsified signal to a memory of the wearable sensor device, and
    transmitting the stored sampled sparsified signal to the base station in response to determining that the wireless communication connection has been established.

15. The monitoring system of claim 1, wherein the electronic processor of the wearable sensor device is configured to apply the transformation to generate the sparsified signal by applying a band stop filter to the quasi-periodic signal.

16. The monitoring system of claim 1, wherein the electronic processor of the wearable sensor device is configured to sample the sparsified signal by applying compressive sensing to the sparsified signal.

17. The monitoring system of claim 1, wherein the electronic processor of the wearable sensor device is configured to apply the transformation to sparsify the quasi-periodic signal by applying a transformation to generate a sparsified signal that exhibits sparcity in a non-linear domain.

18. A method for sensing and recovering a quasi-periodic signal, the method comprising:
applying a transformation to sparsify the quasi-periodic signal removing morphology parameters and leaving temporal parameters;
sampling the sparsified signal;
transmitting the sampled signal data to a base station;
recovering the sparsified signal from the sampled sparsified signal data;
determining the temporal parameters of the quasi-periodic signal from the recovered sparsified signal;
generating a reconstructed signal shape using previously captured morphology parameters; and
generating a reconstructed signal by adjusting and scaling the reconstructed signal shape based on the determined temporal parameters.

19. The method of claim 18, wherein the quasi-periodic signal includes a physiologic signal, the method further comprising detecting the quasi-periodic signal using a wearable sensor device.

20. The method of claim 19, wherein the quasi-periodic signal includes an ECG signal, wherein applying the transformation includes filtering the ECG signal to leave only R-peaks of the ECG signal in the sparsified signal, and wherein recovering the temporal parameters of the quasi-periodic signal from the sampled signal data includes determining a frequency of R-peaks in the ECG signal from the recovered sparsified signal.

21. The method of claim 20, wherein generating the reconstructed signal shape using previously captured morphology parameters includes accessing a previously stored ECG signal shape from a computer-readable memory, and wherein generating the reconstructed signal by adjusting and scaling the reconstructed signal shape based on the determined temporal parameters includes adjusting and scaling the previously stored ECG signal shape based on the determined frequency of the R-peaks in the ECG signal.

22. The method of claim 18, wherein applying the transformation to sparsify the quasiperiodic signal includes applying a band stop filter to the quasi-periodic signal.

23. The method of claim 18, wherein applying the transformation to sparsify the quasiperiodic signal includes applying the transformation to generate a sparsified signal that exhibited sparcity in a non-linear domain.

* * * * *